US012661071B2

(12) United States Patent
Liu et al.

(10) Patent No.: US 12,661,071 B2
(45) Date of Patent: Jun. 23, 2026

(54) METHOD AND APPARATUS FOR CLASSIFYING ELECTROENCEPHALOGRAM SIGNAL, METHOD AND APPARATUS FOR TRAINING CLASSIFICATION MODEL, AND ELECTRONIC DEVICE AND COMPUTER-READABLE STORAGE MEDIUM

(71) Applicant: Tencent Technology (Shenzhen) Company Limited, Shenzhen (CN)

(72) Inventors: Luyan Liu, Shenzhen (CN); Xiaolin Hong, Shenzhen (CN); Kai Ma, Shenzhen (CN); Yefeng Zheng, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 650 days.

(21) Appl. No.: 17/969,177

(22) Filed: Oct. 19, 2022

(65) Prior Publication Data

US 2023/0054751 A1      Feb. 23, 2023

Related U.S. Application Data

(63) Continuation of application No. PCT/CN2021/106614, filed on Jul. 15, 2021.

(30) Foreign Application Priority Data

Aug. 26, 2020    (CN) ........................ 202010867943.X

(51) Int. Cl.
*A61B 5/00*       (2006.01)
*A61B 5/369*      (2021.01)

(52) U.S. Cl.
CPC ............ *A61B 5/7267* (2013.01); *A61B 5/369* (2021.01); *A61B 5/7275* (2013.01)

(58) Field of Classification Search
CPC .............................. A61B 5/7267; A61B 5/369
(Continued)

(56) References Cited

U.S. PATENT DOCUMENTS 10,209,773 B2 *   2/2019   Khaderi ................. A61B 5/165
2007/0061735 A1 *   3/2007   Hoffberg .............. G06V 40/103
715/744

(Continued)

FOREIGN PATENT DOCUMENTS

CN        104523269 A      4/2015
CN        109770924       *   5/2019
(Continued)

OTHER PUBLICATIONS

Extended European Search Report issued Jun. 30, 2023 in Application No. 21859962.9.
(Continued)

*Primary Examiner* — Nicole F Johnson
(74) *Attorney, Agent, or Firm* — Sughrue Mion, PLLC

(57)        ABSTRACT

A method and an apparatus for classifying an electroencephalogram signal, a device and a computer-readable storage medium. The method includes: obtaining an electroencephalogram signal; performing feature extraction on the electroencephalogram signal to obtain a signal feature corresponding to the electroencephalogram signal; obtaining a difference distribution ratio, the difference distribution ratio being used for representing impacts of difference distributions of different types on distributions of the signal feature and a source domain feature in a feature domain, the source domain feature being a feature corresponding to a source domain electroencephalogram signal; aligning the signal
(Continued)

Computer system 100 feature with the source domain feature according to the difference distribution ratio to obtain an aligned signal feature; and classifying the aligned signal feature to obtain a motor imagery type corresponding to the electroencephalogram signal.

20 Claims, 8 Drawing Sheets

(58) Field of Classification Search
USPC ........................................................ 600/301
See application file for complete search history.

(56) References Cited

U.S. PATENT DOCUMENTS

2011/0071965 A1    3/2011   Long et al.

2019/0073605 A1     3/2019   Keller
2019/0150727 A1*    5/2019   Blaha ................... A61B 3/0091

FOREIGN PATENT DOCUMENTS

| CN | 110851783 A | | 2/2020 |
|---|---|---|---|
| CN | 202010364697 | * | 4/2020 |
| CN | 111544856 A | | 8/2020 |
| CN | 111584029 A | | 8/2020 |
| CN | 111728609 A | | 10/2020 |
| WO | 2020/023989 A1 | | 2/2020 |

OTHER PUBLICATIONS

Chinese Office Action for 202010867943.X dated Oct. 13, 2020.
International Search Report for PCT/CN2021/106614 dated Oct. 12, 2021.
Written Opinion for PCT/CN2021/106614 dated Oct. 12, 2021.

* cited by examiner

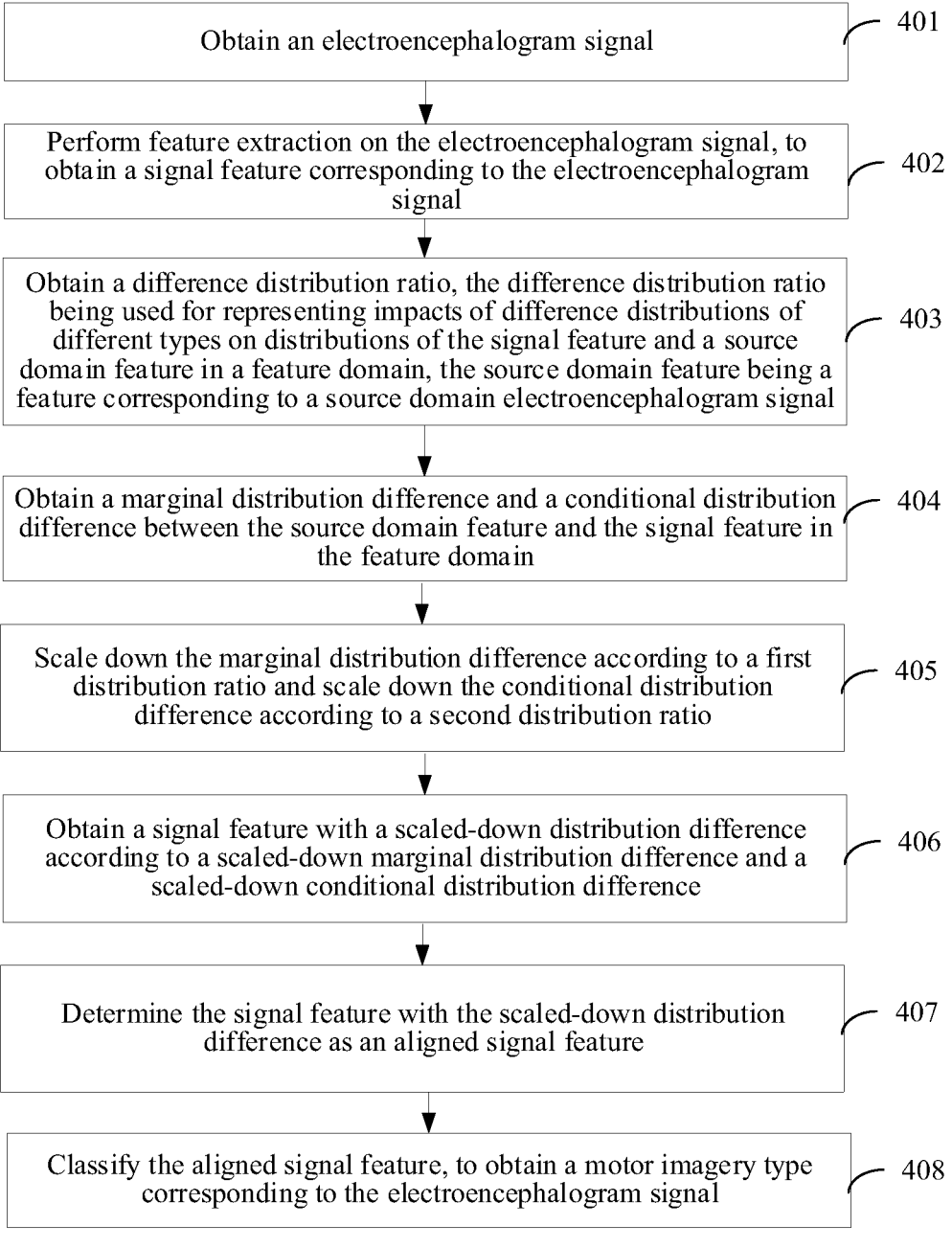

Obtain an electroencephalogram signal — 401

Perform feature extraction on the electroencephalogram signal, to obtain a signal feature corresponding to the electroencephalogram signal — 402

Obtain a difference distribution ratio, the difference distribution ratio being used for representing impacts of difference distributions of different types on distributions of the signal feature and a source domain feature in a feature domain, the source domain feature being a feature corresponding to a source domain electroencephalogram signal — 403

Obtain a marginal distribution difference and a conditional distribution difference between the source domain feature and the signal feature in the feature domain — 404

Scale down the marginal distribution difference according to a first distribution ratio and scale down the conditional distribution difference according to a second distribution ratio — 405

Obtain a signal feature with a scaled-down distribution difference according to a scaled-down marginal distribution difference and a scaled-down conditional distribution difference — 406

Determine the signal feature with the scaled-down distribution difference as an aligned signal feature — 407

Classify the aligned signal feature, to obtain a motor imagery type corresponding to the electroencephalogram signal — 408

FIG. 4

Obtain a source domain electroencephalogram signal and a target domain electroencephalogram signal ⌐ 601

Perform feature extraction on the source domain electroencephalogram signal and the target domain electroencephalogram signal, to obtain a source domain feature corresponding to the source domain electroencephalogram signal and a target domain feature corresponding to the target domain electroencephalogram signal ⌐ 602

Obtain a difference distribution ratio, the difference distribution ratio being used for representing impacts of difference distributions of different types on distributions of the source domain feature and the target domain feature in a feature domain ⌐ 603

Align the source domain feature with the target domain feature in the feature domain according to the difference distribution ratio, to obtain an aligned target domain feature ⌐ 604

Classify the aligned target domain feature, and train an electroencephalogram signal classification model according to a classification result, to obtain a trained electroencephalogram signal classification model ⌐ 605

FIG. 6

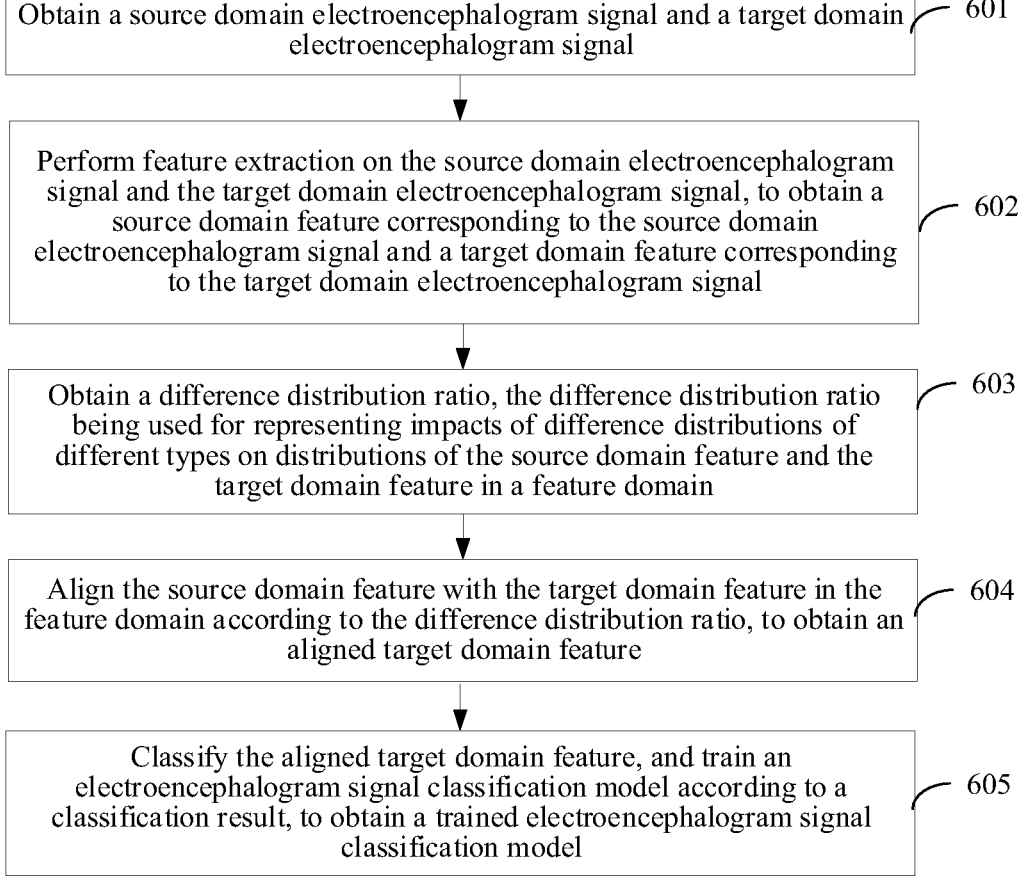

FIG. 7

METHOD AND APPARATUS FOR CLASSIFYING ELECTROENCEPHALOGRAM SIGNAL, METHOD AND APPARATUS FOR TRAINING CLASSIFICATION MODEL, AND ELECTRONIC DEVICE AND COMPUTER-READABLE STORAGE MEDIUM

CROSS-REFERENCE TO RELATED APPLICATION(S)

This application is a continuation application of International Application No. PCT/CN2021/106614 filed on Jul. 15, 2021, which claims priority to Chinese Patent Application No. 202010867943.X filed with the China National Intellectual Property Administration on Aug. 26, 2020, the disclosures of which are incorporated by reference in their entireties.

FIELD

The present disclosure relates to the field of transfer learning, and in particular, to a method and an apparatus for classifying an electroencephalogram signal, a method and an apparatus for training a classification model, and a computer-readable storage medium.

BACKGROUND

Electroencephalogram signals are electrical signals generated by neurons during brain activity. Motor imagery types corresponding to the electroencephalogram signals may be recognized by using the electroencephalogram signals. That is, limb movement implemented by a brain through "ideas" is recognized.

The electroencephalogram signal may be applied to the medical field, for example, applied to be combined with a medical technology. Medical staff detects a lesion region of a patient according to an electroencephalogram signal and by using a cloud platform for medical and health services created through "cloud computing". An electroencephalogram signal acquisition device is usually connected to a computer device (an external device) by a brain computer interface (BCI), and a motor imagery type represented by an electroencephalogram signal outputted by the brain computer interface is recognized by using the external device (for example, the computer device), to implement direct control of a brain on an object. Electroencephalogram signals of different individuals are greatly different, an electroencephalogram signal classification model needs to be separately trained for an electroencephalogram signal of each individual to ensure that a related mode can correctly recognize a motor imagery type represented by the electroencephalogram signal.

In the technical solution, the electroencephalogram signal classification model can recognize only an electroencephalogram signal used when the model is trained. Consequently, a use scenario of the electroencephalogram signal classification model is relatively limited without universality.

SUMMARY

The present disclosure provides a method and an apparatus for classifying an electroencephalogram signal, a method and an apparatus for training a classification model, and a computer-readable storage medium. The technical solutions are as follows.

According to an aspect of the disclosure, a method for classifying an electroencephalogram signal, performed by a computer device, may be provided, the method including: obtaining an electroencephalogram signal; performing feature extraction on the electroencephalogram signal, to obtain a signal feature corresponding to the electroencephalogram signal; obtaining a difference distribution ratio, the difference distribution ratio being used for representing impacts of difference distributions of different types on distributions of the signal feature and a source domain feature in a feature domain, the source domain feature being a feature corresponding to a source domain electroencephalogram signal, and schematically, the source domain electroencephalogram signal being a sample electroencephalogram signal used when an electroencephalogram signal classification model is trained; aligning the signal feature with the source domain feature according to the difference distribution ratio, to obtain an aligned signal feature; and classifying the aligned signal feature, to obtain a motor imagery type corresponding to the electroencephalogram signal.

According to another aspect of the disclosure, a method for training an electroencephalogram signal classification model, performed by a computer device, may be provided, the method including: obtaining a source domain electroencephalogram signal and a target domain electroencephalogram signal; performing feature extraction on the source domain electroencephalogram signal and the target domain electroencephalogram signal, to obtain a source domain feature corresponding to the source domain electroencephalogram signal and a target domain feature corresponding to the target domain electroencephalogram signal;
obtaining a difference distribution ratio, the difference distribution ratio being used for representing impacts of difference distributions of different types on distributions of the source domain feature and the target domain feature in a feature domain; aligning the source domain feature with the target domain feature in the feature domain according to the difference distribution ratio, to obtain an aligned target domain feature; and classifying the aligned target domain feature, and training an electroencephalogram signal classification model according to a classification result, to obtain a trained electroencephalogram signal classification model.

According to another aspect of the disclosure, an apparatus for classifying an electroencephalogram signal may be provided, including: a first obtaining module, configured to obtain an electroencephalogram signal; a first feature extraction module, configured to perform feature extraction on the electroencephalogram signal to obtain a signal feature corresponding to the electroencephalogram signal; the first obtaining module, configured to obtain a difference distribution ratio, the difference distribution ratio being used for representing impacts of difference distributions of different types on distributions of the signal feature and a source domain feature in a feature domain, the source domain feature being a feature corresponding to a source domain electroencephalogram signal; schematically, the source domain electroencephalogram signal being a sample electroencephalogram signal used when an electroencephalogram signal classification model is trained; a first processing module, configured to align the signal feature with the source domain feature according to the difference distribution ratio, to obtain an aligned signal feature; and a classification module, configured to classify the aligned signal feature, to obtain a motor imagery type corresponding to the electroencephalogram signal.

According to another aspect of the disclosure, an apparatus for training an electroencephalogram signal classification model may be provided, including: a second obtaining module, configured to obtain a source domain electroencephalogram signal and a target domain electroencephalogram signal; a second feature extraction module, configured to perform feature extraction on the source domain electroencephalogram signal and the target domain electroencephalogram signal, to obtain a source domain feature corresponding to the source domain electroencephalogram signal and a target domain feature corresponding to the target domain electroencephalogram signal; the second obtaining module, configured to obtain a difference distribution ratio, the difference distribution ratio being used for representing impacts of difference distributions of different types on distributions of the source domain feature and the target domain feature in a feature domain; a second processing module, configured to align the source domain feature with the target domain feature in the feature domain according to the difference distribution ratio, to obtain an aligned target domain feature; and a training module, configured to classify the aligned target domain feature, and train an electroencephalogram signal classification model according to a classification result, to obtain a trained electroencephalogram signal classification model.

According to another aspect of the disclosure, a computer device may be provided, including a processor and a memory, the memory storing at least one instruction, at least one program, a code set or an instruction set, the at least one instruction, the at least one program, the code set or the instruction set being loaded and executed by the processor to implement the method for classifying an electroencephalogram signal and the method for training an electroencephalogram signal classification model according to the foregoing aspects.

According to another aspect of the disclosure, a non-transitory computer-readable storage medium may be provided, storing at least one instruction, at least one program, a code set or an instruction set, the at least one instruction, the at least one program, the code set or the instruction set being loaded and executed by a processor to implement the method for classifying an electroencephalogram signal and the method for training an electroencephalogram signal classification model according to the foregoing aspects.

According to another aspect of the disclosure, a computer program product or a computer program may be provided, the computer program product or the computer program including computer instructions, the computer instructions being stored in a computer-readable storage medium. A processor of the computer device may be configured to read the computer instructions from the computer-readable storage medium and executes the computer instructions to cause the computer device to perform the method for classifying an electroencephalogram signal and the method for training an electroencephalogram signal classification model according to the foregoing aspects.

The technical solutions provided in the embodiments of the disclosure include at least the following beneficial effects:

A distribution of a signal feature corresponding to an electroencephalogram signal in a feature domain is dynamically adjusted according to a difference distribution ratio, to align the signal feature of the electroencephalogram signal with a source domain feature, so as to ensure that the signal feature of the electroencephalogram signal is close to the source domain feature in terms of feature distribution. An electroencephalogram signal classification model trained based on the source domain feature can transfer a classification method to the signal feature corresponding to the electroencephalogram signal, which improves the accuracy of recognition by the electroencephalogram signal classification model on a motor imagery type corresponding to the electroencephalogram signal, so that the electroencephalogram signal classification model can recognize a plurality of types of electroencephalogram signals, thereby achieving universality.

BRIEF DESCRIPTION OF THE DRAWINGS

To describe the technical solutions in the embodiments of the disclosure more clearly, the following briefly describes the accompanying drawings required for describing the embodiments. The accompanying drawings in the following description show merely some embodiments of the disclosure, and a person skilled in the art may still derive other drawings from these accompanying drawings without creative efforts. In addition, one of ordinary skill would understand that aspects of example embodiments may be combined together or implemented alone.

FIG. 4 is a flowchart of a method for classifying an electroencephalogram signal according to another example embodiment of the disclosure.

FIG. 6 is a flowchart of a method for training an electroencephalogram signal classification model according to an example embodiment of the disclosure.

FIG. 7 is a frame diagram of a method for training an electroencephalogram signal classification model according to an example embodiment of the disclosure.

DESCRIPTION OF EMBODIMENTS

Figure 1:
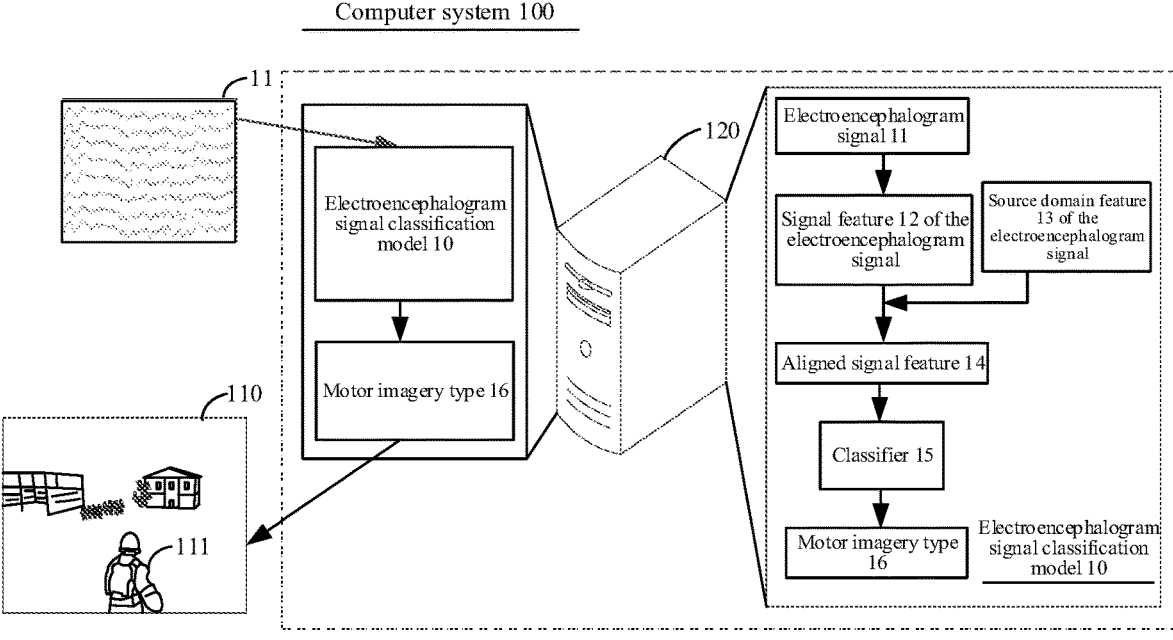
FIG. 1 is a frame diagram of a computer system according to an example embodiment of the disclosure.

To make the objectives, technical solutions, and advantages of the disclosure clearer, the disclosure is further described in detail below with reference to the accompanying drawings. It is to be understood that the described embodiments are not to be considered as a limitation to the disclosure, and all other embodiments obtained by a person of ordinary skill in the art without creative efforts shall fall within the protection scope of the present disclosure.

Electroencephalogram (EEG) signal refers to an electrical signal generated by each neuron during brain activity, and collectively reflects an electrophysiological activity of a brain neural cell on a cerebral cortex or a scalp surface. A biological voltage of a brain is acquired by using an invasive or non-invasive brain computer interface device to obtain an electroencephalogram signal, and a curve is drawn by using the electroencephalogram signal, to obtain an electroencephalogram. By analyzing the electroencephalogram signal, activation effects of different brain regions are detected and recognized to determine a user intention, to implement communication and control between a human brain and an external device. In the embodiments of the disclosure, a description is made by using an example in which the non-invasive brain computer interface device acquires the biological voltage of the brain.

Motor imagery (MI) refers to a thinking process in which a person imagines normal movement of limbs through a brain, where a movement process is imagined or rehearsed repeatedly to control limb movement by using "ideas", and is a spontaneous electroencephalogram signal. Common motor imagery parts are a left hand, a right hand, feet, and a tongue.

Brain computer interface (BCI) is a connection path established when a brain of a person or an animal exchanges information with the external device. For example, a BCI system combined with an electric wheelchair controls a movement direction of the electric wheelchair by acquiring an electroencephalogram signal of a user to help the user with physical disabilities to travel freely.

Domain adaptation learning (DAL) is a machine learning theory that can resolve a problem that a probability of a training sample is inconsistent with a probability distribution of a test sample. In a conventional machine learning algorithm, it is usually assumed that a training sample (a source domain) and a test sample (a target domain) are from a same probability distribution, and a corresponding model and a discrimination criterion are constructed to predict a to-be-tested sample. However, in some scenarios, the test sample and the training sample are not from the same probability distribution, and a case that a probability distribution of the source domain is inconsistent with a probability distribution of the target domain may be resolved through the DAL. In the DAL, the source domain is an existing knowledge or a learned knowledge of a model; and the target domain is a to-be-learned knowledge of the model.

Medical Cloud is a cloud platform for medical and health services created by using "cloud computing" based on new technologies such as cloud computing, a mobile technology, multimedia, 4G communication, big data, and Internet of Things in combination with a medical technology to share medical resources and enlarge a medical range. Due to application and combination of the cloud computing technology, the medical cloud improves the efficiency of a medical institution and facilitates residents to see a doctor. For example, pre-registration, an electronic medical record, and health insurance are products of the combination of cloud computing and the medical field. The medical cloud further has the advantages of data security, information sharing, dynamic expansion, and overall layout. A method for classifying an electroencephalogram signal provided in the embodiments of the disclosure may be combined with the cloud platform for medical and health services. Medical staff uploads electroencephalogram signals of a plurality of patients and motor imagery types corresponding to the electroencephalogram signals to the cloud platform for reference by other medical staff during diagnosis and treatment.

Cloud gaming, also referred to as a gaming on demand, is an online gaming technology based on the cloud computing technology. The cloud gaming technology enables a thin client with relatively limited graphics processing and data computing capabilities to run a high-quality game. In a cloud gaming scenario, the game is run on the cloud server rather than a game terminal of a player, and the cloud server renders the game scenario into a video and audio stream, and transmits the video and audio stream to the game terminal of the player by using the network. The game terminal of the player is not required to have powerful graphics computing and data processing capabilities, but only required to have a basic streaming media playback capability and the capability of acquiring instructions inputted by the player and sending the instructions to the cloud server. The method for classifying an electroencephalogram signal provided in the embodiments of the disclosure may be combined with the cloud gaming. A motor imagery type corresponding to an electroencephalogram signal is recognized to control a game character in the cloud gaming to move.

The method for classifying an electroencephalogram signal provided in the embodiments of the disclosure may be applicable to the following scenarios.

1. Smart Medical Care

In this application scenario, the method for classifying an electroencephalogram signal provided in the embodiments of the disclosure may be applicable to BCI systems of some medical instruments or rehabilitation robots.

For example, an electroencephalogram signal of a patient suffering from hemiplegia or cerebral stroke is inputted into a BCI system of an exoskeleton robot. The BCI system of the exoskeleton robot recognizes the electroencephalogram signal of the patient according to the method for classifying an electroencephalogram signal provided in the embodiments of the disclosure and determines a motor imagery type to which the electroencephalogram signal belongs to drive the exoskeleton robot to help the patient to perform active rehabilitation.

In another example, an electroencephalogram signal of a user with physical disabilities is inputted into a BCI system of an electric wheelchair. The BCI system of the electric wheelchair recognizes the electroencephalogram signal of the user with physical disabilities according to the method for classifying an electroencephalogram signal provided in the embodiments of the disclosure and determines a motor imagery type to which the electroencephalogram signal belongs to control the electric wheelchair to move according to the motor imagery type, thereby helping the user with physical disabilities to travel freely.

2. Control of a Virtual Role in a Game Application

In this application scenario, the method for classifying an electroencephalogram signal provided in the embodiments of the disclosure may be applicable to a backend server at a game application side. A dynamic domain adaptation model is constructed in the backend server. An electroencephalogram signal of a user is obtained, and a motor imagery type to which the electroencephalogram signal of the user belongs is determined so that a virtual role in a game is driven to perform various activities in a virtual environment according to the motor imagery type. For example, in a virtual reality application, a user wears a head mounted device with an electroencephalogram signal acquisition function so that the user can control a virtual role in the virtual reality application through "ideas".

A description is made by using only the two application scenarios as examples. However, the method provided in the embodiments of the disclosure may be further applicable to other scenarios in which an object needs to be controlled by using an electroencephalogram signal (for example, a scenario in which a cause of disease of a patient is analyzed by using an electroencephalogram signal). A specific application scenario is not limited in the embodiments of the disclosure.

The method for classifying an electroencephalogram signal and a method for training an electroencephalogram signal classification model provided in the embodiments of the disclosure may be applicable to a computer device with a data processing capability. For example, the method for classifying an electroencephalogram signal and the method for training an electroencephalogram signal classification model provided in the embodiments of the disclosure may be applicable to a personal computer, a workstation, or a server, that is, an electroencephalogram signal may be classified and an electroencephalogram signal classification model may be trained by using the personal computer, the workstation, or the server. It is assumed that the computer device performing the method for classifying an electroencephalogram signal is a first computer device, and the computer device for performing the method for training an electroencephalogram signal classification model is a second computer device, the first computer device and the second computer device may be a same device or may be different devices.

The trained electroencephalogram signal classification model may be implemented as a part of an application and is installed in a terminal so that when receiving an electroencephalogram signal, the terminal recognizes a motor imagery type corresponding to the electroencephalogram signal. Alternatively, the trained electroencephalogram signal classification model is set in a backend server of an application, so that a terminal in which the application is installed implements a function of recognizing a motor imagery type corresponding to an electroencephalogram signal by using the backend server.

FIG. 1 is a schematic diagram of a computer system 100 according to an example embodiment of the disclosure. The computer system 100 includes a terminal 110 and a server 120. The terminal 110 and the server 120 perform data communication with each other through a communication network. The communication network may be a wired network or a wireless network, and the communication network may be at least one of a local area network, a metropolitan area network, or a wide area network.

An application that supports an electroencephalogram signal recognition function is installed in the terminal 110. The application may be a virtual reality (VR) application, an augmented reality (AR) application, a medical application, a game application, or the like. This is not limited in this embodiment of the disclosure.

Further, the terminal 110 may be a mobile terminal such as a mobile phone, a smartwatch, a tablet computer, a laptop portable notebook computer, or an intelligent robot, or may be a terminal such as a desktop computer or a projection computer, or may be a terminal such as an exoskeleton robot, an electric wheelchair, or a head mounted display. A type of the terminal is not limited in this embodiment of the disclosure.

The server 120 may be an independent physical server, or may be a server cluster or a distributed system formed by a plurality of physical servers, or may be a cloud server that provides basic cloud computing services such as a cloud service, a cloud database, cloud computing, a cloud function, cloud storage, a network service, cloud communication, a middleware service, a domain name service, a security service, a content delivery network (CDN), big data, and an AI platform. In an example embodiment, the server 120 is a backend server of the application in the terminal 110.

As shown in FIG. 1, in this embodiment, a game application is run in the terminal 110, and a user controls a virtual role 111 in the game application by using an electroencephalogram signal 11. The user wears an electroencephalogram signal acquisition device such as an electroencephalogram signal acquisition helmet for acquiring an electroencephalogram signal. The electroencephalogram signal acquisition device is an invasive or non-invasive signal acquisition device. The electroencephalogram signal acquisition device is connected to the terminal 110, and when the electroencephalogram signal acquisition device acquires the electroencephalogram signal 11 of the user, the terminal records the electroencephalogram signal 11 of the user and sends the electroencephalogram signal 11 of the user to the server 120. An electroencephalogram signal classification model 10 is established in the server 120, and the electroencephalogram signal classification model 10 is a trained machine learning model.

When receiving the electroencephalogram signal 11 of the user, the electroencephalogram signal classification model 10 extracts a signal feature 12 of the electroencephalogram signal and aligns the signal feature 12 with a source domain feature 13 of a source domain electroencephalogram signal used when the electroencephalogram signal classification model 10 is trained, so that the signal feature 12 is close to the source domain feature 13 in a feature domain to obtain an aligned signal feature 14. Therefore, the electroencephalogram signal classification model 10 performs transferring according to a domain adaptation learning method so that the electroencephalogram signal classification model 10 is suitable for recognizing the current electroencephalogram signal 11. The aligned signal feature 14 is inputted into a classifier 15 of the electroencephalogram signal classification model 10, and a motor imagery type 16 corresponding to the electroencephalogram signal 11 is outputted. The motor imagery type 16 includes at least one of forward movement, backward movement, lying prone, squatting, shooting, throwing, or driving a virtual carrier.

The server 120 generates a control instruction according to the motor imagery type 16 and sends the control instruction to the terminal 110. The terminal 110 controls, according to the control instruction, the virtual role 111 to perform an activity corresponding to the motor imagery type 16.

In an example, a user wears an electroencephalogram signal acquisition helmet and the user imagines controlling a virtual role 111 to run forward. The electroencephalogram signal acquisition helmet sends an acquired electroencephalogram signal 11 to the terminal 110, and the terminal 110 sends the electroencephalogram signal 11 to the server 120. The electroencephalogram signal classification model 10 recognizes that a motor imagery type 16 of the electroencephalogram signal 11 is running forward, the server 120 generates a control instruction of running forward according to the motor imagery type 16 of running forward and sends the control instruction to the terminal 110, and the terminal 110 displays a picture in which the virtual role 111 runs forward so that the user controls the virtual role 111 by using the electroencephalogram signal 11.

In some embodiments, the electroencephalogram signal acquisition device is connected to the server 120. The electroencephalogram signal classification model is established in the server 120. The electroencephalogram signal acquisition device directly inputs the acquired electroencephalogram signal 11 to the server 120. In some other embodiments, the electroencephalogram signal classification model is established in the terminal 110. The terminal 110 receives the acquired electroencephalogram signal 11 and recognizes the electroencephalogram signal 11.

It may be understood that only the game application in the terminal is used as an example in the foregoing embodiment. In an actual use process, the electroencephalogram signal classification model may further be established in a driving system of a robot with a rehabilitation function and in a driving system of an electric wheelchair. Motor imagery types corresponding to electroencephalogram signals are different for different application scenarios. This is not limited in this embodiment of the disclosure.

For ease of description, a description is made by using an example in which a method for classifying an electroencephalogram signal and a method for training an electroencephalogram signal classification model are performed by the server in the following embodiments. However, the two methods may alternatively be performed by the terminal, that is, the two methods may be performed by a computer device.

Figure 2:
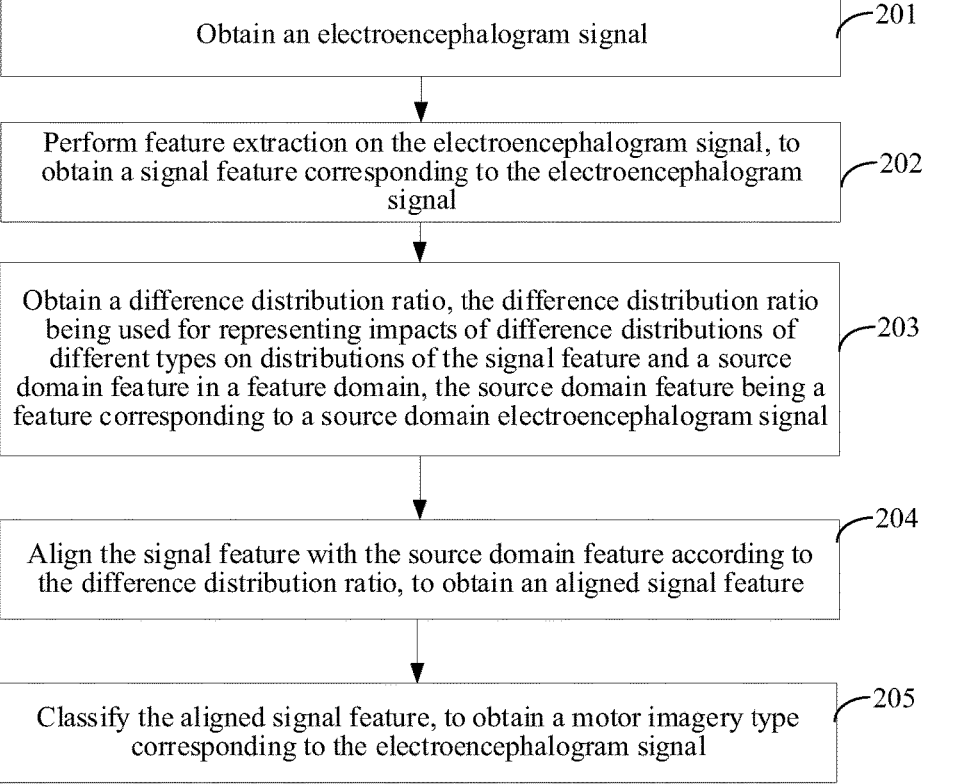
FIG. 2 is a flowchart of a method for classifying an electroencephalogram signal according to an example embodiment of the disclosure.

FIG. 2 is a flowchart of a method for classifying an electroencephalogram signal according to an example embodiment of the disclosure. In this embodiment, a description is made by using an example in which the method is applicable to the server 120 in the computer system 100 shown in FIG. 1. The method includes the following operations.

Operation 201. Obtain an electroencephalogram signal.

The electroencephalogram signal refers to an electrical signal generated by each neuron during brain activity, and collectively reflects an electrophysiological activity of a brain nerve cell on a cerebral cortex or a scalp surface. The electroencephalogram signal may be obtained by an electroencephalogram signal acquisition device.

Obtaining manners of the electroencephalogram signal are classified according to the electroencephalogram signal acquisition device and include an invasive obtaining manner and a non-invasive obtaining manner. In the invasive obtaining manner, a micro-electrode needs to be implanted into nerve cortical of a person through surgery to collect potential information of a single neuron or local nerve cortical. The non-invasive obtaining manner is a non-invasive nerve activity information obtaining manner. A detection electrode is attached to a brain to acquire an electroencephalogram signal. A subject (that is, a person of which an electroencephalogram signal is acquired) wears an electroencephalogram signal acquisition device such as an electroencephalogram signal acquisition helmet, or an electrode is attached to a head of the subject to acquire the electroencephalogram signal.

Electroencephalogram signal images of different types are generated according to different electroencephalogram signal acquisition manners, for example, at least one of an electroencephalography (EEG), functional magnetic resonance imaging (fMRI), a near-infrared spectroscopy (NIRS), or a magnetoencephalography (MEG).

In some embodiments, the electroencephalogram signal acquisition device is in communication connection with the server. The electroencephalogram signal acquisition device sends an acquired electroencephalogram signal to the server. In some other embodiments, the electroencephalogram signal acquisition device is in communication connection with a terminal used by a user. The terminal is in communication connection with the server, the terminal records and stores the acquired electroencephalogram signal, and the terminal sends the electroencephalogram signal to the server. In some other embodiments, the electroencephalogram signal acquisition device is in communication connection with the terminal used by the user. The terminal records and stores the acquired electroencephalogram signal, and the terminal recognizes the electroencephalogram signal. This is not limited in this embodiment of the disclosure.

Operation 202. Perform feature extraction on the electroencephalogram signal to obtain a signal feature corresponding to the electroencephalogram signal.

Figure 3:
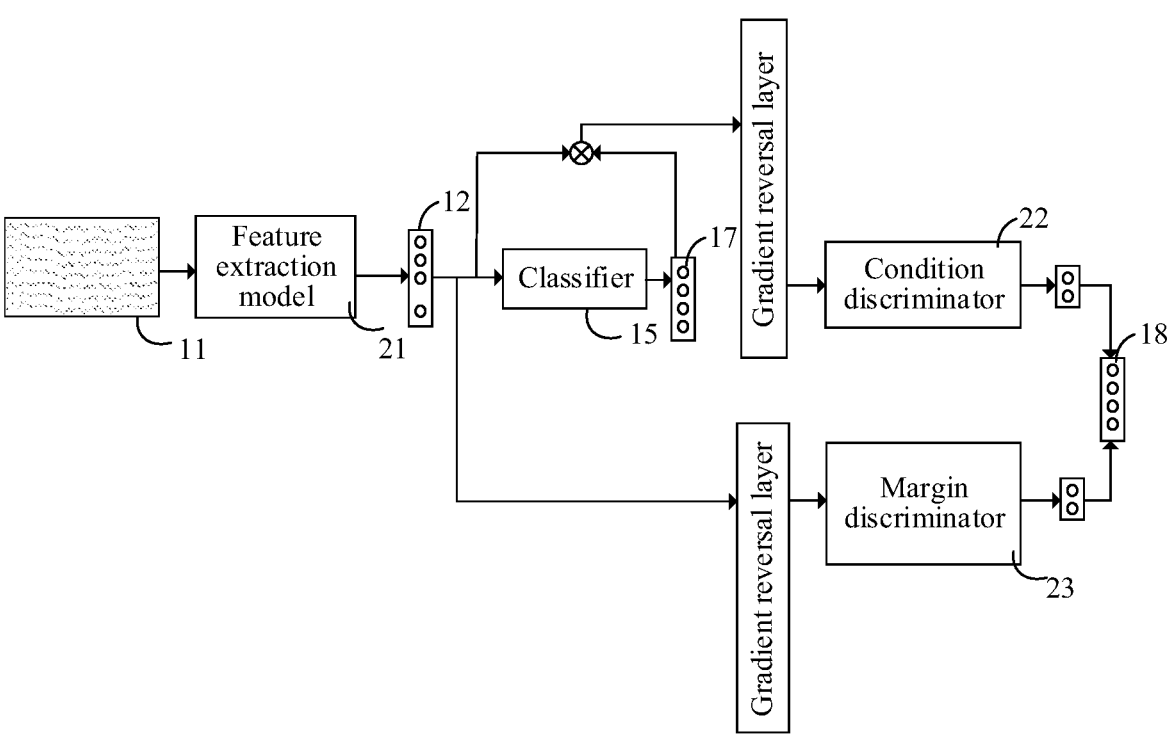
FIG. 3 is a schematic structural diagram of an electroencephalogram signal classification model according to an example embodiment of the disclosure.

As shown in FIG. 3, an electroencephalogram signal classification model is established in the server 120. The electroencephalogram signal classification model includes a feature extraction model 21. A signal feature 12 corresponding to an electroencephalogram signal 11 is extracted by using the feature extraction model 21. In some embodiments, before the electroencephalogram signal 11 is inputted into the feature extraction model, the electroencephalogram signal further needs to be pre-processed to remove an artifact and interference from the electroencephalogram signal, so as to reduce an impact of noise on the electroencephalogram signal.

The signal feature 12 that is not easily observed and detected of the inputted electroencephalogram signal 11 is extracted by using the feature extraction model 21, so that the electroencephalogram signal classification model can accurately classify the signal feature 12. The signal feature 12 of the electroencephalogram signal includes: a time domain feature and a spatial domain feature. The time domain feature refers to a change of the electroencephalogram signal over time, and the spatial domain feature refers to a change of the electroencephalogram signal in different brain regions. In some embodiments, the signal feature 12 of the electroencephalogram signal further includes a frequency domain feature. The frequency domain feature refers to a change of the electroencephalogram signal in frequency. In this embodiment of the disclosure, a description is made by using an example in which the signal feature of the electroencephalogram signal includes the time domain feature and the spatial domain feature.

Operation 203. Obtain a difference distribution ratio, the difference distribution ratio being used for representing impacts of difference distributions of different types on distributions of the signal feature and a source domain feature in a feature domain, the source domain feature being a feature corresponding to a source domain electroencephalogram signal.

The source domain feature is a signal feature corresponding to a source domain electroencephalogram signal. The source domain electroencephalogram signal is a sample electroencephalogram signal used when the electroencephalogram signal classification model is trained. In this embodiment, the electroencephalogram signal is a test electroencephalogram signal used when the electroencephalogram signal classification model is tested (or is used).

Since different subjects have great differences, distributions of electroencephalogram signals of different subjects are different in a same time domain and spatial domain, and distributions of electroencephalogram signals of a same subject are different in the same time domain or spatial domain under different states or emotions, that is, different electroencephalogram signals have a distribution difference in a feature domain. For example, aspects such as a physical status and an emotion status of a subject 1 are close to that of a subject 2. An electroencephalogram signal of the subject 1 reaches a peak value from the 4th second to the 6th second, and an electroencephalogram signal of the subject 2 reaches a peak value from the 6th second to the 8th second. In another example, the subject 1 is a young person, and the electroencephalogram signal is always in an active state. The subject 2 is an old person and the electroencephalogram signal is always in a non-active state.

The difference distribution ratio is used for representing impacts of difference distributions of different types on distributions of the signal feature and the source domain feature in the feature domain. In this embodiment of the disclosure, a description is made by using an example in which a difference distribution type includes a conditional distribution difference and a marginal distribution difference. The difference distribution ratio includes a first distribution ratio corresponding to the marginal distribution difference and a second distribution ratio corresponding to the conditional distribution difference. For example, an electroencephalogram signal 1 is a source domain electroencephalogram signal, and an electroencephalogram signal 2 is a test electroencephalogram signal inputted into the electroencephalogram signal classification model. If the electroencephalogram signal 1 is relatively close to the electroencephalogram signal 2, the electroencephalogram signal 1 and the electroencephalogram signal 2 form the conditional distribution difference in the feature domain. If the electroencephalogram signal 1 is greatly different from the electroencephalogram signal 2, the electroencephalogram signal 1 and the electroencephalogram signal 2 form the marginal distribution difference in the feature domain.

Operation 204. Align the signal feature with the source domain feature according to the difference distribution ratio to obtain an aligned signal feature.

Alignment is to make distributions of two different electroencephalogram signals in the feature domain to be the same. An electroencephalogram signal used when the electroencephalogram signal classification model is trained is the source domain electroencephalogram signal, and the electroencephalogram signal classification model can recognize an electroencephalogram signal the same as the source domain electroencephalogram signal. The test electroencephalogram signal used when the electroencephalogram signal classification model is tested is different from the source domain electroencephalogram signal, and when the test electroencephalogram signal is inputted into the electroencephalogram signal classification model, the electroencephalogram signal classification model may classify the test electroencephalogram signal by mistake. When the signal feature is aligned with the source domain feature in the feature domain, the distribution of the signal feature in the feature domain is close to the distribution of the source domain feature in the feature domain so that the electroencephalogram signal classification model correctly classifies the test electroencephalogram signal.

As shown in FIG. 3, the electroencephalogram signal classification model includes a condition discriminator 22 and a margin discriminator 23. The condition discriminator 22 is configured to align the signal feature 12 of the electroencephalogram signal with the source domain feature in the feature domain according to the second distribution ratio corresponding to the conditional distribution difference. The margin discriminator 23 is configured to align the signal feature 12 of the electroencephalogram signal with the source domain feature in the feature domain according to the first distribution ratio corresponding to the marginal distribution difference. The condition discriminator 22 and the margin discriminator 23 may simultaneously align the signal feature 12 with the source domain feature in the feature domain according to the respective distribution ratios.

Operation 205. Classify the aligned signal feature to obtain a motor imagery type corresponding to the electroencephalogram signal.

Since the distribution of the signal feature of the electroencephalogram signal is close to the distribution of the source domain feature in the feature domain, the electroencephalogram signal classification model transfers a method for classifying the source domain feature to the signal feature in a transfer learning manner, so that the electroencephalogram signal classification model can accurately classify the electroencephalogram signal.

As shown in FIG. 3, the electroencephalogram signal classification model includes a classifier 15. The classifier 15 is configured to classify the signal feature 12 of the electroencephalogram signal and comprehensively output a prediction probability 18 of a motor imagery type in combination with the condition discriminator 22 and the margin discriminator 23. Motor imagery refers to a thinking process in which a person imagines normal movement of limbs through a brain, that is, the person imagines that the limbs are moving, but the limbs are actually not moving. According to different application scenarios, a common motor imagery type includes at least one of movement of hands, movement of feet, or movement of a tongue (swallowing). Schematically, the motor imagery type is used for indicating limb movement imagined in the electroencephalogram signal.

Based on the foregoing, according to the method provided in this embodiment, a distribution of a signal feature corresponding to an electroencephalogram signal in a feature domain is dynamically adjusted according to the difference distribution ratio to align the signal feature of the electroencephalogram signal with a source domain feature, so as to ensure that the signal feature of the electroencephalogram signal is close to the source domain feature in terms of feature distribution. An electroencephalogram signal classification model trained based on the source domain feature can transfer a classification method to the signal feature corresponding to the electroencephalogram signal, which improves the accuracy of recognition by the electroencephalogram signal classification model on a motor imagery type corresponding to the electroencephalogram signal so that the electroencephalogram signal classification model can recognize a plurality of types of electroencephalogram signals, thereby achieving universality.

FIG. 4 is a flowchart of a method for classifying an electroencephalogram signal according to another example embodiment of the disclosure. In this embodiment, a description is made by using an example in which the method is applicable to the server 120 in the computer system 100 shown in FIG. 1. The method includes the following operations.

Operation 401. Obtain an electroencephalogram signal.

In an example embodiment, 22 electroencephalogram electrodes and three electrooculogram electrodes (configured to record electrodes of eye activities) are attached to a head of a subject, a signal sampling rate is 250 Hz, and electroencephalogram signals of four motor imagery types (a left hand, a right hand, feet, and a tongue) are acquired. The quantities of the electroencephalogram electrodes and the electrooculogram electrodes are an exemplary description and may have different values in different embodiments.

The acquired electroencephalogram signals are pre-processed, and an electroencephalogram signal within a time interval corresponding to motor imagery is intercepted from the electroencephalogram signals. In this embodiment of the disclosure, a description is made by using an example in which an electroencephalogram signal between the 2nd second and the 6th second is intercepted. A time of first two seconds is a preparatory stage of data acquisition. In this case, an acquisition device may acquire some noise signals interfering with the electroencephalogram signal or non-electroencephalogram signals. Therefore, interception is performed from the 2nd second to the 6th second.

Subsequently, the three electrooculogram channels are removed from the intercepted electroencephalogram signal, and the 22 electroencephalogram channels are retained. Filtering processing is performed on the electroencephalogram signals in the 22 electroencephalogram channels by using a band-pass filter of a three-order Butterworth filter (a band-pass range is between 0 and 38 Hz), to remove biological artifacts (for example, an eyeball artifact, a muscle artifact, and a cardiac artifact) and noise in some electroencephalogram signals again. The filtered electroencephalogram signals are standardized. For example, the standardization uses the exponentially weighted moving average method, and a weight parameter is set to 0.999, or other standardization such as mean variance standardization or a common spatial patterns (CSP) algorithm may be used.

Operation 402. Perform feature extraction on the electroencephalogram signal, to obtain a signal feature corresponding to the electroencephalogram signal.

Figure 5:
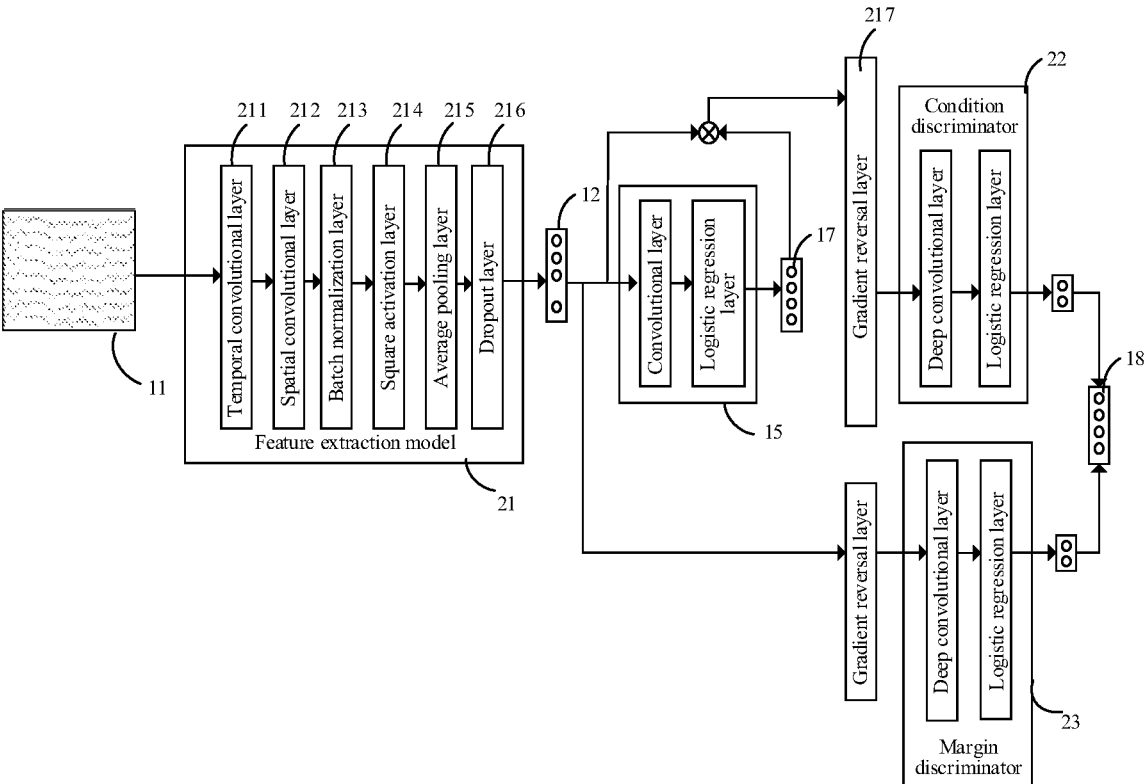
FIG. 5 is a schematic structural diagram of an electroencephalogram signal classification model according to another example embodiment of the disclosure.

As shown in FIG. 5, an electroencephalogram signal classification model includes a feature extraction model 21. The feature extraction model 21 includes a temporal convolutional layer 211, a spatial convolutional layer 212, a batch normalization layer 213, a square activation layer 214, an average pooling layer 215, and a dropout layer 216.

For example, dimensions of the electroencephalogram signal acquired in operation 401 are 1000 dimensions (250*4), and a size of each electroencephalogram signal is 1000*22.

For example, the temporal convolutional layer 211 is invoked to perform feature extraction on the electroencephalogram signal to obtain a first signal feature corresponding to the electroencephalogram signal. The temporal convolutional layer 211 is configured to perform a convolutional operation on the inputted electroencephalogram signal in a time dimension. The spatial convolutional layer 212 is invoked to perform feature extraction on the first signal feature to obtain a second signal feature corresponding to the electroencephalogram signal. The spatial convolutional layer 212 is configured to perform a convolutional operation on the inputted first signal feature in a spatial dimension. The batch normalization layer 213 is invoked to perform feature extraction on the second signal feature to obtain a third signal feature corresponding to the electroencephalogram signal. The square activation layer 214 is invoked to perform feature extraction on the third signal feature to obtain a fourth signal feature corresponding to the electroencephalogram signal. The average pooling layer 215 is invoked to perform feature extraction on the fourth signal feature to obtain a fifth signal feature corresponding to the electroencephalogram signal. The dropout layer 216 is invoked to perform feature extraction on the fifth signal feature to obtain a sixth signal feature corresponding to the electroencephalogram signal. The sixth signal feature is determined as the signal feature corresponding to the electroencephalogram signal, that is, the signal feature finally outputted by the feature extraction model 21.

Table 1 represents parameters of layer structures in the electroencephalogram signal classification model and sizes of signals outputted by the layer structures.

TABLE 1

| Layer structures | Sizes of outputted signals | Model parameters |
| --- | --- | --- |
| Temporal convolutional layer | 40*1000*22 | Convolution kernel size: 25*1, quantity of convolution channels: 40, stride: 1, and padding: 12*0 |
| Spatial convolutional layer | 40*1000*1 | Convolution kernel size: 1*22 (22 is a quantity of electrodes), quantity of convolution channels: 40, and stride: 1 |
| Batch normalization layer | — | — |
| Square activation layer | — | — |
| Average pooling layer | 40*61*1 | Convolution kernel size: 75*1 and stride: 15*1 |
| Dropout layer | — | Drop rate: 0.5 |
| Convolutional layer | 4 | Convolution kernel size: 61*1, stride: 4 |
| Deep convolutional layer | 2 | Convolution kernel size: 61*1, stride: 2 |

The dropout layer refers to that when the electroencephalogram signal classification model performs forward propagation, an activation value of a neuron (a discarded node) stops working with a specific probability. The drop rate is a ratio of a node that is discarded in the dropout layer to total nodes.

Operation 403. Obtain a difference distribution ratio, the difference distribution ratio being used for representing impacts of difference distributions of different types on distributions of the signal feature and a source domain feature in a feature domain, the source domain feature being a feature corresponding to a source domain electroencephalogram signal.

The source domain feature is a signal feature corresponding to a source domain electroencephalogram signal. The source domain electroencephalogram signal is a sample electroencephalogram signal used when the electroencephalogram signal classification model is trained. In this embodiment, the inputted electroencephalogram signal is a test electroencephalogram signal used when the electroencephalogram signal classification model is tested (or is used).

The difference distribution ratio includes a first distribution ratio corresponding to a marginal distribution difference and a second distribution ratio corresponding to a conditional distribution difference. Marginal distribution refers to that random variables (X, Y) exist. A distribution of an event within a range can be described by using a random variable X or a random variable Y. The distribution is usually referred to as a marginal distribution of the random variable X. Conditional distribution refers to that a group of random variables exists. When values of some random variables are determined, distributions of remaining random variables are conditional distributions. For example, an electroencephalogram signal 1 is a source domain electroencephalogram signal, and an electroencephalogram signal 2 is a test electroencephalogram signal inputted into the electroencephalogram signal classification model. If the electroencephalogram signal 1 is relatively close to the electroencephalogram signal 2, the electroencephalogram signal 1 and the electroencephalogram signal 2 form the conditional distribution difference in the feature domain. If the electroencephalogram signal 1 is greatly different from the electroencephalogram signal 2, the electroencephalogram signal 1 and the electroencephalogram signal 2 form the marginal distribution difference in the feature domain.

For example, operation 403 may be implemented into the following operations.

Operation 4031. Obtain a first distribution distance and a second distribution distance between the signal feature and the source domain feature, the first distribution distance being used for representing the marginal distribution difference between the signal feature and source domain feature, and the second distribution distance being used for representing the conditional distribution difference between signal feature and the source domain feature.

The first distribution distance is obtained through calculation according to classification accuracy of a margin discriminator, and the second distribution distance is obtained through calculation according to classification accuracy of a condition discriminator. Reference is made to implementations of operation 4041 to operation 4043.

Operation 4032. Obtain a type quantity of motor imagery types.

In this embodiment of the disclosure, a description is made by using four motor imagery types, that is, the motor imagery types include left hand movement, right hand movement, feet movement, and tongue movement. It may be understood that the motor imagery types are classified according to actual electroencephalogram signals, which are not limited to the four motor imagery types.

It may be understood that operation 4031 and operation 4032 may be performed at the same time, or operation 4031 may be performed before operation 4032, or operation 4032 may be performed before operation 4031.

Operation 4033. Obtain a first distribution ratio corresponding to the marginal distribution difference and a second distribution ratio corresponding to the conditional distribution difference according to the first distribution distance, the second distribution distance, and the type quantity.

Operation 4031 and Operation 4032 are used for calculating the first distribution ratio and the second distribution ratio. A formula for calculating the first distribution ratio is as follows.

$$\mathcal{W} = \frac{d_{A,g}(\mathcal{D}_s^c, \mathcal{D}_t^c)}{d_{A,g}(\mathcal{D}_s^c, \mathcal{D}_t^c) + \frac{1}{C}\sum_{c=1}^{C} d_{A,l}(\mathcal{D}_s^c, \mathcal{D}_t^c)}$$

where $$d_{A,g}(D_s^c, D_t^c)$$

represents the first distribution distance between the source domain feature and the signal feature, $$d_{A,l}(D_s^c, D_t^c)$$

represents the second distribution distance between the source domain feature and the signal feature, C represents the type quantity of motor imagery types, and $\mathcal{W}$ represents importance of a marginal distribution to a distribution difference between the source domain feature and the signal feature in the feature domain.

It can be learned that the second distribution ratio is 1– $\mathcal{W}$, representing importance of a conditional distribution to the distribution difference between the source domain feature and the signal feature in the feature domain.

It may be understood that the first distribution ratio corresponding to the conditional distribution difference may be calculated, and then the first distribution ratio is obtained by using the second distribution ratio.

Operation 404. Obtain the marginal distribution difference and the conditional distribution difference between the source domain feature and the signal feature in the feature domain.

Operation 404 may be replaced with the following operations.

Operation 4041. Obtain first classification accuracy of a margin discriminator and second classification accuracy of a condition discriminator. The margin discriminator being configured to determine a domain signal to which the electroencephalogram signal belongs, the condition discriminator being configured to determine a domain signal to which electroencephalogram signals of different types belong, and the domain signal including at least one of the source domain electroencephalogram signal or an inputted electroencephalogram signal.

The margin discriminator 23 is configured to output a prediction probability that the electroencephalogram signal belongs to a domain signal, that is, output a prediction probability that the electroencephalogram signal belongs to the source domain electroencephalogram signal and a prediction probability that the electroencephalogram signal belongs to the target domain electroencephalogram signal. The source domain electroencephalogram signal is a sample electroencephalogram signal used when the electroencephalogram signal classification model is trained, and the target domain electroencephalogram signal is a test electroencephalogram signal used when the electroencephalogram signal classification model is tested. For example, the margin discriminator 23 outputs the prediction probability of 0.3 that the electroencephalogram signal belongs to the source domain electroencephalogram signal and outputs the prediction probability of 0.7 that the electroencephalogram signal belongs to the target domain electroencephalogram signal. A prediction result is that the inputted electroencephalogram signal belongs to the target domain electroencephalogram signal and is consistent with a type of the inputted electroencephalogram signal. The prediction result outputted by the margin discriminator 23 is correct, and first classification accuracy of the margin discriminator 23 is recorded.

The condition discriminator 22 is configured to output prediction probabilities that electroencephalogram signals of different types belong to a domain signal. The electroencephalogram signals of different types are electroencephalogram signals corresponding to different subjects or electroencephalogram signals of different brain regions of a same subject. For example, the condition discriminator 22 outputs a prediction probability of 0.19 that an electroencephalogram signal of first type belongs to a source domain electroencephalogram signal and outputs a prediction probability of 0.82 that the electroencephalogram signal of first type belongs to a target domain electroencephalogram signal. A prediction result is that the inputted electroencephalogram signal belongs to the target domain electroencephalogram signal and is consistent with a type of the inputted electroencephalogram signal. The prediction result outputted by the condition discriminator 22 is correct, and second classification accuracy of the condition discriminator 22 is recorded.

Operation 4042. Obtain the first distribution distance between the signal feature and the source domain feature according to the first classification accuracy and obtain the second distribution distance between the signal feature and the source domain feature according to the second classification accuracy.

To evaluate impacts of the marginal distribution and the conditional distribution on a cross-domain difference, a distribution difference dynamic evaluation mechanism is introduced to evaluate a difference between two distributions, and an evaluation indicator uses a distance evaluation indicator (A-distance) to measure a distribution difference between a source domain and a target domain. The first distribution distance and the second distribution distance are calculated by using the following formulas.

$$d_{A,g}(\mathcal{D}_s^c, \mathcal{D}_t^c) = 2(1 - 2\epsilon_g^c)$$
$$d_{A,l}(\mathcal{D}_s^c, \mathcal{D}_t^c) = 2(1 - 2\epsilon_l^c)$$

where $$d_{A,g}(D_s^c, D_t^c)$$

represents the first distribution distance between the source domain feature and the signal feature, $$d_{A,l}(D_s^c, D_t^c)$$

represents the second distribution distance between the source domain feature and the signal feature, $$\epsilon_g^c$$

represents the first classification accuracy corresponding to the margin discriminator, and $$\epsilon_l^c$$

represents the second classification accuracy corresponding to the condition discriminator.

Operation 4043. Determine the first distribution distance as the marginal distribution difference and determine the second distribution distance as the conditional distribution difference.

The first distribution distance $$d_{A,g}(D_s^c, D_t^c)$$

is determined as the marginal distribution difference, and the second distribution distance $$d_{A,l}(D_s^c, D_t^c)$$

is determined as the conditional distribution difference.

Operation 405. Scale down the marginal distribution difference according to the first distribution ratio and scale down the conditional distribution difference according to the second distribution ratio.

When the signal feature is aligned with the source domain feature in the feature domain, the conditional distribution difference and the marginal distribution difference are scaled down simultaneously. The marginal distribution difference and the conditional distribution difference are respectively adjusted according to the first distribution ratio and the second distribution ratio.

Operation 406. Obtain a signal feature with a scaled-down distribution difference according to a scaled-down marginal distribution difference and a scaled-down conditional distribution difference.

The conditional distribution and the marginal distribution of the signal feature in the feature domain are aligned with the source domain feature, to obtain an aligned signal feature. A distribution difference between the signal feature and the source domain feature is scaled down.

Operation 407. Determine the signal feature with the scaled-down distribution difference as an aligned signal feature.

In this case, the distribution of the signal feature in the feature domain is close to the distribution of the source domain feature in the same feature domain.

Operation 408. Classify the aligned signal feature, to obtain a motor imagery type corresponding to the electroencephalogram signal.

Operation 408 may be replaced with the following operations.

Operation 4081. Invoke a classifier to process the aligned signal feature, to obtain a prediction probability of the motor imagery type corresponding to the electroencephalogram signal, the motor imagery type including at least one of movement of hands, movement of feet, or movement of a tongue.

As shown in FIG. 5, the signal feature corresponding to the electroencephalogram signal outputted by the feature extraction model 21 is respectively inputted into the classifier 15, the condition discriminator 22, and the margin discriminator 23. The classifier 15 includes a convolutional layer (a convolutional neural network, C-Conv or CNN) and a logistic regression layer (softmax). The convolutional layer performs convolution processing on the signal feature and outputs an intermediate vector. The intermediate vector is inputted into the logistic regression layer, and the prediction probability of the motor imagery type corresponding to the electroencephalogram signal is outputted. For example, a prediction probability of left hand movement outputted by the classifier 15 is 0.2, a prediction probability of right hand movement is 0.7, a prediction probability of movement of feet is 0, and a prediction probability of tongue movement is 0.1.

A feature vector outputted by the classifier 15 is inputted into a gradient reversal layer (GRL) 217. The gradient reversal layer 217 performs further calculation to obtain another feature vector. The another feature vector is respectively inputted into the condition discriminator 22 and the margin discriminator 23. The gradient reversal layer 217 is configured to multiply an error transmitted to the layer by a negative number $(-\lambda)$, so that training targets of network layers before and after the gradient reversal layer are opposite, to achieve a confrontation effect.

Operation 4082. Invoke the condition discriminator to process the aligned signal feature, to obtain the prediction probabilities that the electroencephalogram signals of different types belong to the domain signal, the domain signal including at least one of the source domain electroencephalogram signal or the inputted electroencephalogram signal.

As shown in FIG. 5, the condition discriminator 22 includes a deep convolutional layer (a deep convolutional neural network, D-Conv or DCNN) and a logistic regression layer. The deep convolutional layer performs convolution processing on the signal feature and outputs an intermediate vector. The intermediate vector is inputted into the logistic regression layer, and prediction probabilities that electroencephalogram signals of different types belong to a domain signal are outputted. Types of electroencephalogram signals may be classified according to subjects of different types or according to different brain regions or according to emotions (or states) of a subject. For example, a prediction probability that an electroencephalogram signal of a first type belongs to the source domain electroencephalogram signal outputted by the condition discriminator 22 is 0.7, and an outputted prediction probability that the electroencephalogram signal of the first type belongs to the target domain electroencephalogram signal is 0.3, so that the electroencephalogram signal of the first type belongs to the source domain electroencephalogram signal. The electroencephalogram signal of the first type is classified according to electroencephalogram signals generated by different brain regions.

Operation 4083. Invoke the margin discriminator to process the aligned signal feature to obtain the prediction probability that the electroencephalogram signal belongs to the domain signal.

As shown in FIG. 5, the margin discriminator 23 includes a deep convolutional layer and a logistic regression layer. The deep convolutional layer performs convolution processing on the signal feature and outputs an intermediate vector. The intermediate vector is inputted into the logistic regression layer, and the prediction probability that the electroencephalogram signal belongs to the domain signal is outputted. A difference between the margin discriminator 23 and the condition discriminator 22 is that the margin discriminator 23 determines only the domain signal to which the electroencephalogram signal belongs.

Operation 4081, operation 4082, and operation 4083 are performed simultaneously.

Operation 4084. Obtain the motor imagery type corresponding to the electroencephalogram signal according to the prediction probability of the motor imagery type corresponding to the electroencephalogram signal, the prediction probabilities that the electroencephalogram signals of different types belong to the domain signal, and the prediction probability that the electroencephalogram signal belongs to the domain signal.

The distribution difference dynamic evaluation mechanism is introduced to evaluate the difference between the two distributions, a distribution with a significant impact is aligned preferentially, and the condition discriminator 22 and the margin discriminator 23 determine respective distribution ratios. Therefore, when the electroencephalogram signal classification model outputs the motor imagery type, the motor imagery type is obtained comprehensively according to the output results of the classifier 15, the condition discriminator 22, and the margin discriminator 23.

Based on the foregoing, according to the method provided in this embodiment, a distribution of a signal feature corresponding to an electroencephalogram signal in a feature domain is dynamically adjusted according to a difference distribution ratio to align the signal feature of the electroencephalogram signal with a source domain feature, so as to ensure that the signal feature of the electroencephalogram signal is close to the source domain feature in terms of feature distribution. An electroencephalogram signal classification model trained based on the source domain feature can transfer a classification method to the signal feature corresponding to the electroencephalogram signal, which improves the accuracy of recognition by the electroencephalogram signal classification model on a motor imagery type corresponding to the electroencephalogram signal, so that the electroencephalogram signal classification model can recognize a plurality of types of electroencephalogram signals, thereby achieving universality.

A distribution difference between the signal feature and the source domain feature that are inputted into the electroencephalogram signal classification model is dynamically adjusted according to a first distribution ratio corresponding to a marginal distribution difference and a second distribution ratio corresponding to a conditional distribution difference, so that the signal feature is accurately close to the source domain feature, thereby ensuring that the electroencephalogram signal classification model can accurately obtain an aligned signal feature.

A first distribution distance and a second distribution distance between the source domain feature and the signal feature are determined according to first classification accuracy of a margin discriminator and second classification accuracy of a condition discriminator, so that the electroencephalogram signal classification model determines the marginal distribution difference and the conditional distribution difference according to the first distribution distance and the second distribution distance.

The first distribution distance and the second distribution distance between the signal feature and the source domain feature respectively represent the marginal distribution difference and the conditional distribution difference between the signal feature and the source domain feature, so that the first distribution ratio corresponding to the marginal distribution difference and the second distribution ratio corresponding to the conditional distribution difference are accurately calculated according to a type quantity of motor imagery types.

The aligned signal feature is processed by invoking a classifier, the margin discriminator, and the condition discriminator, and a motor imagery classification model corresponding to the electroencephalogram signal is obtained comprehensively according to prediction probabilities outputted by the classifier, the margin discriminator, and the condition discriminator, so that the electroencephalogram signal classification model can recognize electroencephalogram signals of different types, to improve accuracy of the motor imagery type outputted by the electroencephalogram signal classification model.

The signal feature of the electroencephalogram signal is outputted by invoking each layer structure in a feature extraction model, so that the signal feature of the electroencephalogram signal has time invariance, and subsequently the electroencephalogram signal classification model outputs an accurate motor imagery type.

The following describes the method for training an electroencephalogram signal classification model.

FIG. 6 is a flowchart of a method for training an electroencephalogram signal classification model according to an example embodiment of the disclosure. In this embodiment, a description is made by using an example in which the method is applicable to the server 120 in the computer system 100 shown in FIG. 1. The method includes the following operations.

Operation 601. Obtain a source domain electroencephalogram signal and a target domain electroencephalogram signal.

The source domain electroencephalogram signal is a sample electroencephalogram signal used when an electroencephalogram signal classification model is trained, and the target domain electroencephalogram signal is a test electroencephalogram signal used when the electroencephalogram signal classification model is tested. The electroencephalogram signal classification model is trained by using a public dataset. The public dataset includes a training set and a test set. For example, public competition data such as a public motor imagery dataset of the BCI competition IV dataset 2a is used. The dataset includes nine subjects, electroencephalogram data of each subject is recorded by using 22 electroencephalogram electrodes and three electrooculogram electrodes, a signal sampling rate is 205 Hz, and four motor imagery types (left hand movement, right hand movement, feet movement, and tongue movement) are included.

As shown in FIG. 7, the entire training process of the electroencephalogram signal classification model is the same as the use process, including: inputting an electroencephalogram signal 701, pre-processing the electroencephalogram signal 702, introducing a distribution difference dynamic evaluation mechanism 703 into an electroencephalogram signal classification model 704, and outputting a prediction result 705. The pre-processing 702 includes bandpass filtering 7021 and signal standardization 7022. In some embodiments, the electroencephalogram signal classification model is also referred to as a dynamic domain adaptation model.

For the pre-processing process of the electroencephalogram signal, reference is made to the implementation of operation 401. Details are not described herein again.

Operation 602. Perform feature extraction on the source domain electroencephalogram signal and the target domain electroencephalogram signal, to obtain a source domain feature corresponding to the source domain electroencephalogram signal and a target domain feature corresponding to the target domain electroencephalogram signal.

Figure 8:
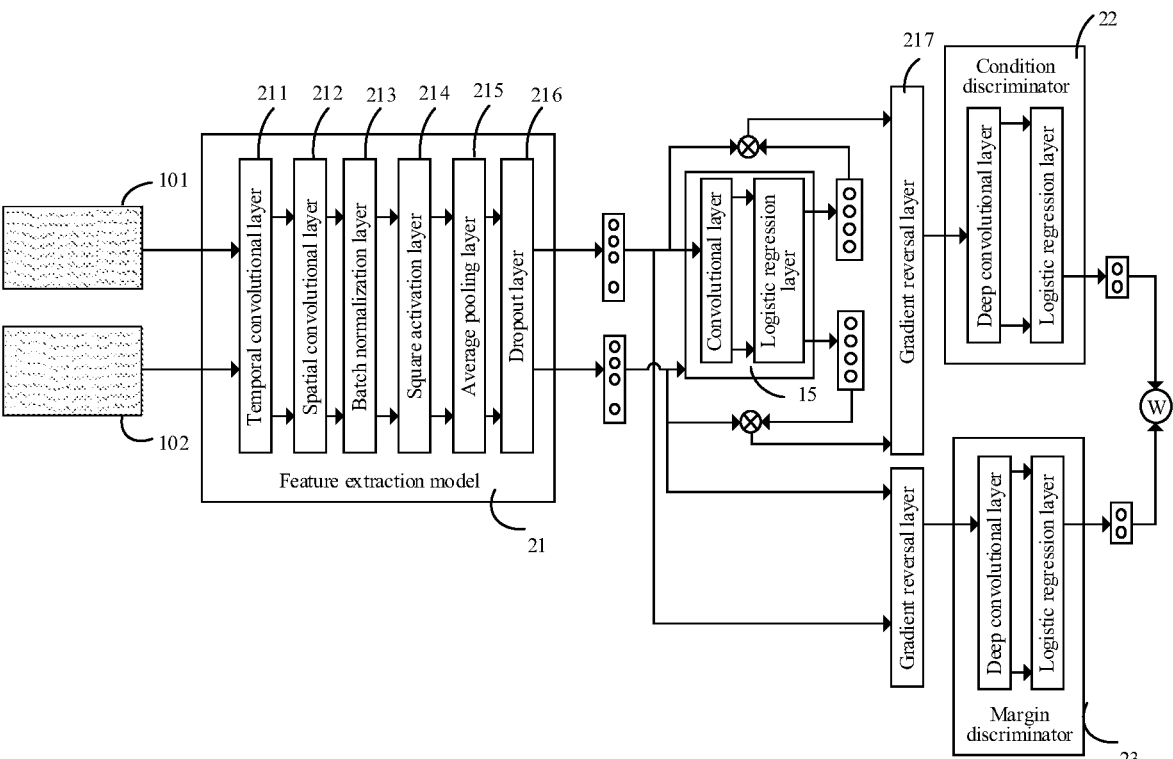
FIG. 8 is a schematic structural diagram of an electroencephalogram signal classification model according to another example embodiment of the disclosure.

As shown in FIG. 8, a source domain electroencephalogram signal 101 and a target domain electroencephalogram signal 102 are inputted into a feature extraction model 21 in the electroencephalogram signal classification model 704, and then a source domain feature corresponding to the source domain electroencephalogram signal and a target domain feature corresponding to the target domain electroencephalogram signal are outputted by using each layer of the feature extraction model 21. Reference is made to the implementation of operation 402 and details are not described herein again.

Operation 603. Obtain a difference distribution ratio, the difference distribution ratio being used for representing impacts of difference distributions of different types on distributions of the source domain feature and the target domain feature in a feature domain.

The difference distribution ratio includes a first distribution ratio corresponding to a marginal distribution difference and a second distribution ratio corresponding to a conditional distribution difference.

The distributions of the target domain feature and the source domain feature in the feature domain are different. Therefore, to evaluate the impact of difference distributions of different types on the source domain feature and the target domain feature, a distribution difference dynamic evaluation mechanism is introduced to evaluate the marginal distribution difference and the conditional distribution difference between the source domain feature and the target domain feature. A difference distribution with a relatively large impact is dynamically adjusted according to distribution ratios respectively corresponding to the marginal distribution difference and the conditional distribution difference.

Operation 604. Align the source domain feature with the target domain feature in the feature domain according to the difference distribution ratio, to obtain an aligned target domain feature.

Operation 604 may be replaced with the following operations.

Operation 6041. Obtain a marginal distribution difference and a conditional distribution difference between the source domain feature and the target domain feature in the feature domain.

First classification accuracy of a margin discriminator and second classification accuracy of a condition discriminator are obtained. The first margin discriminator is configured to determine a domain signal to which the electroencephalogram signal belongs, and the condition discriminator is configured to determine, according to a motor imagery type, a domain signal to which the electroencephalogram signal belongs. The domain signal includes at least one of the source domain electroencephalogram signal or the target domain electroencephalogram signal. A first distribution distance between the target domain feature and the source domain feature is obtained according to the first classification accuracy and a second distribution distance between the target domain feature and the source domain feature is obtained according to the second classification accuracy. The first distribution distance is determined as the marginal distribution difference, and the second distribution distance is determined as the conditional distribution difference.

Reference is made to the implementations of operation 4041 to operation 4043 and details are not described herein again.

Operation 6042. Scale down the marginal distribution difference according to the first distribution ratio and scale down the conditional distribution difference according to the second distribution ratio.

Operation 6043. Obtain a target domain feature with a scaled-down distribution difference according to a scaled-down marginal distribution difference and a scaled-down conditional distribution difference.

Operation 6044. Determine the target domain feature with the scaled-down distribution difference as the aligned target domain feature.

For implementations of operation 6041 to operation 6043, reference is made to the implementations of operation 404 to operation 407 and details are not described herein again.

Operation 605. Classify the aligned target domain feature, and train an electroencephalogram signal classification model according to a classification result, to obtain a trained electroencephalogram signal classification model.

Operation 605 may be replaced with the following operations.

Operations 6051. Invoke a classifier, a margin discriminator, and a condition discriminator in the electroencephalogram signal classification model to respectively process the aligned target domain feature, to obtain a prediction probability of a motor imagery type corresponding to the target domain electroencephalogram signal.

As shown in FIG. 8, a classifier 15, a margin discriminator 23, and a condition discriminator 22 simultaneously process, according to the distribution difference dynamic evaluation mechanism, a source domain feature and a target domain feature that are outputted by the feature extraction model. Because a distribution of the source domain feature is close to a distribution of the target domain feature in the feature domain, the electroencephalogram signal classification model may transfer a method for classifying the source domain feature to the target domain feature, so that the electroencephalogram signal classification model obtains a motor imagery type corresponding to the target domain electroencephalogram signal.

A feature vector outputted by the classifier 15 is inputted into a gradient reversal layer (GRL) 217. The gradient reversal layer 217 performs further calculation, to obtain another feature vector. The another feature vector is respectively inputted into the condition discriminator 22 and the margin discriminator 23. The gradient reversal layer 217 is configured to multiply an error transmitted to the layer by a negative number ($-\lambda$), so that training targets of network layers before and after the gradient reversal layer are opposite, to achieve a confrontation effect.

Operation 6052. Calculate a result error of the electroencephalogram signal classification model according to the prediction probability and a real label of the motor imagery type corresponding to the electroencephalogram signal.

The result error includes an error corresponding to the classifier, an error corresponding to the condition discriminator, and an error corresponding to the margin discriminator. In this embodiment of the disclosure, an example in which the result error is calculated by using an error function is used, and the following respectively describes calculation manners of the three errors.

1. The Error Corresponding to the Classifier

A first loss function corresponding to the classifier is calculated according to the prediction probability and the real label. A formula is as follows.

$$L_c(\theta_f, \theta_c) = \mathbb{E}_{(x_i^s, y_i^s) \sim D_s} L(p_i^s, y_i^s)$$

where $L_c(\theta_f, \theta_c)$ represents the first loss function corresponding to the classifier, $$\mathbb{E}_{(x_i^s, y_i^s)}$$

represents an expected value of the source domain feature, $$x_i^s$$

represents the source domain electroencephalogram signal, $$y_i^s$$

represents a prediction probability of the source domain electroencephalogram signal, $D_s$ represents a source domain, $L(\ )$ represent a cross entropy loss function, $$p_i^s$$

represents a real label of the source domain electroencephalogram signal, and "~" represents a belonging relationship. The formula represents that the source domain electroencephalogram signal and the real label corresponding to the source domain electroencephalogram signal are obtained from a source domain electroencephalogram signal dataset, and an expectation of a classification loss of the source domain electroencephalogram signal is calculated.

2. The Error Corresponding to the Condition Discriminator

A second loss function corresponding to the condition discriminator is calculated according to a source domain condition feature map corresponding to the source domain feature and a target domain condition feature map corresponding to the target domain feature that are outputted by the condition discriminator. A formula is as follows.

$$L_l(\theta_t, \theta_l) = -\mathbb{E}_{x_i^s \sim D_s} \log[D_c(g_i^s)] - \mathbb{E}_{x_j^t \sim D_t} \log[1 - D_c(g_j^t)]$$

where $$g_i^s$$

represents the source domain condition feature map, $$g_j^t$$

represents the target domain condition feature map, $D_c$ represents a $c^{th}$-type condition discriminator, that is, a source domain electroencephalogram signal and a target domain electroencephalogram signal that belong to a $c^{th}$-type are inputted into the condition discriminator for classification, $D_s$ represents the source domain, $D_t$ represent a target domain, $$\mathbb{E}_{x_i^s}$$

represents the expected value of the source domain feature, $$\mathbb{E}_{x_j^t}$$

represents an expected value of the target domain feature, and "~" represents the belonging relationship.

A calculation manner of the condition feature map is as follows.

A prediction probability of the classifier is set to $f=[f_1, f_2, f_3 \ldots f_d]$, and a feature map is $p=[p_1, p_2, p_3 \ldots p_d]$, so that the condition feature map g is the following matrix.

$$\begin{bmatrix} p_1 \cdot f_1 & p_2 \cdot f_1 & \cdots & p_d \cdot f_1 \\ p_1 \cdot f_2 & p_2 \cdot f_2 & \cdots & p_d \cdot f_2 \\ \vdots & \vdots & & \ddots \\ p_1 \cdot f_d & p_2 \cdot f_d & \cdots & p_d \cdot f_d \end{bmatrix}$$

3. The Error Corresponding to the Margin Discriminator

A third loss function corresponding to the margin discriminator is calculated according to a source domain feature map corresponding to the source domain feature and a target domain feature map corresponding to the target domain feature that are outputted by the margin discriminator. A formula is as follows.

$$L_g(\theta_f, \theta_g) = -\mathbb{E}_{x_i^s \sim \mathcal{D}_s} \log[D_m(G(x_i^s))] - \mathbb{E}_{x_j^t \sim \mathcal{D}_t} \log[1 - D_m(G(x_j^t))]$$

where $$x_i^s$$

represents the source domain feature map, $$x_j^t$$

represents the target domain feature map, G(x) represents a feature extraction model, $D_m$ represents the margin discriminator, $D_s$ represents the source domain, a represent the target domain, $$\mathbb{E}_{x_j^t}.$$

represents the expected value of the source domain feature, $$\mathbb{E}_{x_j^t}$$

represents the expected value of the target domain feature, and "~" represents the belonging relationship.

Based on the foregoing, a total result error is the following error.

$$L(\theta_j, \theta_c, \theta_d, \theta_d^c|_{c=1}^C) = L_c - \alpha(\mathcal{W}L_9 + (1 - \mathcal{W})L_l)$$

where $L_c$ represents the first loss function of the classifier, α represents a to-be-learned parameter of the electroencephalogram signal classification model, $L_g$ represents the third loss function corresponding to the margin discriminator, Li represents the second loss function corresponding to the condition discriminator, $\mathcal{W}$ represents importance of a marginal distribution to a distribution difference between the source domain feature and the signal feature in the feature domain, and C represent a type quantity of motor imagery types.

Operation 6053. Train the electroencephalogram signal classification model according to the result error and by using an error back propagation algorithm to obtain the trained electroencephalogram signal classification model.

An error backpropagation (BP) algorithm refers to that an output error is propagated backward layer by layer to an input layer through a hidden layer in a particular form, and the error is allocated to all units in each layer to obtain an error signal of each layer. The error signal is a basis of correcting a unit weight. A learning process of a machine learning model is formed by two processes of forward propagation and error backward propagation. During forward propagation, an input sample is inputted from an input layer and propagated to an output layer after being processed by hidden layers layer by layer. If an actual output of the output layer is inconsistent with an expected output, an error backward propagation stage is entered.

In this embodiment of the disclosure, a parameter of a neural network model is resolved by using a gradient descent method based on stochastic gradient descent (SGD), and the model parameter is initialized by using a Xavier initialization method. During resolution, an electroencephalogram signal of each subject and a corresponding label are transmitted into a network for learning, and model optimization is completed through error backward propagation.

Based on the foregoing, according to the method provided in this embodiment, a distribution of a target domain feature in a feature domain is dynamically adjusted according to a difference distribution ratio, to align the target domain feature with a source domain feature, so as to train an electroencephalogram signal classification model based on an aligned target domain feature, so that the electroencephalogram signal classification model can transfer a classification learning method to the target domain feature, and the trained electroencephalogram signal classification model can accurately output a motor imagery type corresponding to an electroencephalogram signal and recognize a plurality of types of electroencephalogram signals, thereby achieving universality.

A distribution difference between the target domain feature and the source domain feature that are inputted into the electroencephalogram signal classification model is dynamically adjusted according to a first distribution ratio corresponding to a marginal distribution difference and a second distribution ratio corresponding to a conditional distribution difference, so that the target domain feature is accurately close to the source domain feature, thereby ensuring that the electroencephalogram signal classification model can accurately obtain an aligned target domain feature.

A first distribution distance and a second distribution distance between the source domain feature and the target domain feature are determined according to first classification accuracy of a margin discriminator and second classification accuracy of a condition discriminator, so that the electroencephalogram signal classification model determines the marginal distribution difference and the conditional distribution difference according to the first distribution distance and the second distribution distance.

The aligned target domain feature is processed by using a classifier, the margin discriminator, and the condition discriminator, and the electroencephalogram signal classification model is trained by using a real label of the motor imagery type corresponding to the electroencephalogram signal and an error between prediction probabilities outputted by the electroencephalogram signal classification model, to ensure that the electroencephalogram signal classification model may accelerate convergence, thereby shortening a training time of the model.

A result error of the electroencephalogram signal classification model is accurately calculated according to a first loss function corresponding to the classifier, a second loss function corresponding to the margin discriminator, and a third loss function corresponding to the condition discriminator, so that the electroencephalogram signal classification model is trained based on the accurate result error to improve a convergence speed of the model, thereby shortening the training time of the model.

Figures 9, 10:
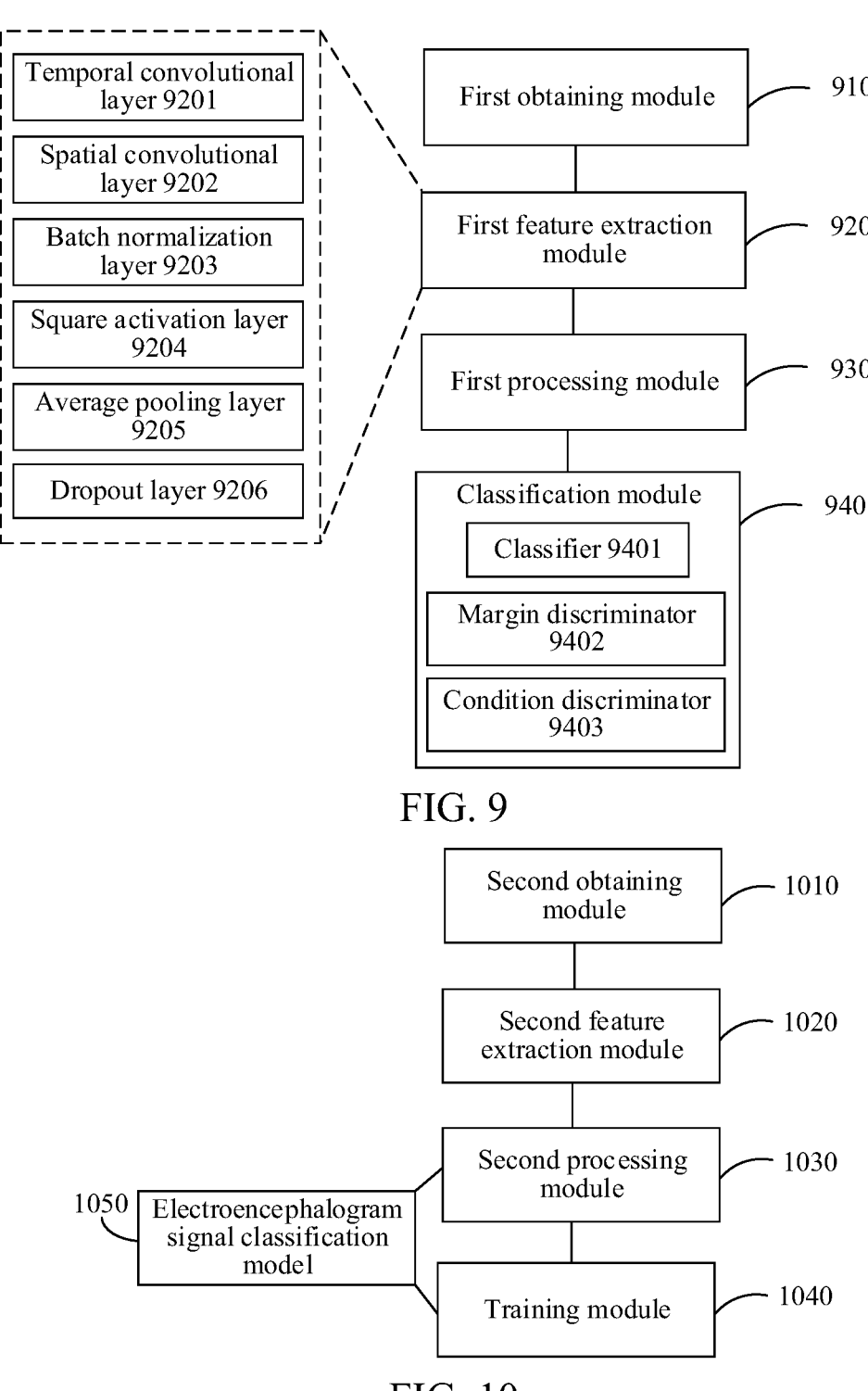
FIG. 9 is a structural block diagram of an apparatus for classifying an electroencephalogram signal according to an example embodiment of the disclosure.
FIG. 10 is a structural block diagram of an apparatus for training an electroencephalogram signal classification model according to an example embodiment of the disclosure.

FIG. 9 is a structural block diagram of an apparatus for classifying an electroencephalogram signal according to an example embodiment of the disclosure. The apparatus may be implemented as an entire computer device or a part of the computer device. The apparatus includes the following modules, or code:

a first obtaining module 910 configured to obtain an electroencephalogram signal;

a first feature extraction module 920 configured to perform feature extraction on the electroencephalogram signal to obtain a signal feature corresponding to the electroencephalogram signal;

the first obtaining module 910 being configured to obtain a difference distribution ratio, the difference distribution ratio being used for representing impacts of difference distributions of different types on distributions of the signal feature and a source domain feature in a feature domain, the source domain feature being a feature corresponding to a source domain electroencephalogram signal;

a first processing module 930 configured to align the signal feature with the source domain feature according to the difference distribution ratio, to obtain an aligned signal feature; and a classification module 940 configured to classify the aligned signal feature to obtain a motor imagery type corresponding to the electroencephalogram signal.

In an example embodiment, the difference distribution ratio may include a first distribution ratio corresponding to a marginal distribution difference and a second distribution ratio corresponding to a conditional distribution difference.

The first obtaining module 910 is configured to obtain the marginal distribution difference and the conditional distribution difference between the source domain feature and the signal feature in the feature domain.

The first processing module 930 is configured to scale down the marginal distribution difference according to the first distribution ratio and scale down the conditional distribution difference according to the second distribution ratio; obtain a signal feature with a scaled-down distribution difference according to a scaled-down marginal distribution difference and a scaled-down conditional distribution difference; and determine the signal feature with the scaled-down distribution difference as the aligned signal feature.

In an example embodiment, the first obtaining module 910 may be configured to obtain first classification accuracy of a margin discriminator and second classification accuracy of a condition discriminator, the margin discriminator being configured to determine a domain signal to which the electroencephalogram signal belongs, the condition discriminator being configured to determine a domain signal to which electroencephalogram signals of different types belong, and the domain signal including at least one of the source domain electroencephalogram signal or an inputted electroencephalogram signal; obtain a first distribution distance between the signal feature and the source domain feature according to the first classification accuracy and obtain a second distribution distance between the signal feature and the source domain feature according to the second classification accuracy; and determine the first distribution distance as the marginal distribution difference, and determine the second distribution distance the conditional distribution difference.

In an example embodiment, the difference distribution ratio may include the first distribution ratio corresponding to the marginal distribution difference and the second distribution ratio corresponding to the conditional distribution difference.

The first obtaining module 910 is configured to obtain the first distribution distance and the second distribution distance between the signal feature and the source domain feature, the first distribution distance being used for representing the marginal distribution difference between the signal feature and source domain feature, and the second distribution distance being used for representing the conditional distribution difference between signal feature and the source domain feature; obtain a type quantity of motor imagery types; and obtain the first distribution ratio corresponding to the marginal distribution difference and the second distribution ratio corresponding to the conditional distribution difference according to the first distribution distance, the second distribution distance, and the type quantity.

In an example embodiment, the classification module 940 may include a classifier 9401, a condition discriminator 9402, and a margin discriminator 9403.

The classifier 9401 is configured to process the aligned signal feature to obtain a prediction probability of the motor imagery type corresponding to the electroencephalogram signal. The motor imagery type includes at least one of movement of hands, movement of feet, or movement of a tongue.

The condition discriminator 9402 is configured to process the aligned signal feature to obtain prediction probabilities that the electroencephalogram signals of different types belong to the domain signal, the domain signal including at least one of the source domain electroencephalogram signal or the inputted electroencephalogram signal.

The margin discriminator 9403 is configured to process the aligned signal feature to obtain a prediction probability that the electroencephalogram signal belongs to the domain signal.

The classification module 940 is configured to obtain the motor imagery type corresponding to the electroencephalogram signal according to the prediction probability of the motor imagery type corresponding to the electroencephalogram signal, the prediction probabilities that the electroencephalogram signals of different types belong to the domain signal, and the prediction probability that the electroencephalogram signal belongs to the domain signal.

In an example embodiment, the first feature extraction module 920 may include a temporal convolutional layer 9201, a spatial convolutional layer 9202, a batch normalization layer 9203, a square activation layer 9204, an average pooling layer 9205, and a dropout layer 9206.

The temporal convolutional layer 9201 is configured to perform feature extraction on the electroencephalogram signal to obtain a first signal feature corresponding to the electroencephalogram signal.

The spatial convolutional layer 9202 is configured to perform feature extraction on the first signal feature to obtain a second signal feature corresponding to the electroencephalogram signal.

The batch normalization layer 9203 is configured to perform feature extraction on the second signal feature to obtain a third signal feature corresponding to the electroencephalogram signal.

The square activation layer 9204 is configured to perform feature extraction on the third signal feature to obtain a fourth signal feature corresponding to the electroencephalogram signal.

The average pooling layer 9205 is configured to perform feature extraction on the fourth signal feature to obtain a fifth signal feature corresponding to the electroencephalogram signal.

The dropout layer 9206 is configured to perform feature extraction on the fifth signal feature to obtain a sixth signal feature corresponding to the electroencephalogram signal and determine the sixth signal feature as the signal feature corresponding to the electroencephalogram signal.

Based on the foregoing, according to the apparatus provided in this embodiment, a distribution of a signal feature corresponding to an electroencephalogram signal in a feature domain is dynamically adjusted according to a difference distribution ratio to align the signal feature of the electroencephalogram signal with a source domain feature, so as to ensure that the signal feature of the electroencephalogram signal is close to the source domain feature in terms of feature distribution. An electroencephalogram signal classification model trained based on the source domain feature can transfer a classification method to the signal feature corresponding to the electroencephalogram signal, which improves the accuracy of recognition by the electroencephalogram signal classification model on a motor imagery type corresponding to the electroencephalogram signal, so that the electroencephalogram signal classification model can recognize a plurality of types of electroencephalogram signals, thereby achieving universality.

A distribution difference between the signal feature and the source domain feature that are inputted into the electroencephalogram signal classification model is dynamically adjusted according to a first distribution ratio corresponding to a marginal distribution difference and a second distribution ratio corresponding to a conditional distribution difference, so that the signal feature is accurately close to the source domain feature, thereby ensuring that the electroencephalogram signal classification model can accurately obtain an aligned signal feature.

A first distribution distance and a second distribution distance between the source domain feature and the signal feature are determined according to first classification accuracy of a margin discriminator and second classification accuracy of a condition discriminator, so that the electroencephalogram signal classification model determines the marginal distribution difference and the conditional distribution difference according to the first distribution distance and the second distribution distance.

The first distribution distance and the second distribution distance between the signal feature and the source domain feature respectively represent the marginal distribution difference and the conditional distribution difference between the signal feature and the source domain feature, so that the first distribution ratio corresponding to the marginal distribution difference and the second distribution ratio corresponding to the conditional distribution difference are accurately calculated according to a type quantity of motor imagery types.

The aligned signal feature is processed by invoking a classifier, the margin discriminator, and the condition discriminator, and a motor imagery classification model corresponding to the electroencephalogram signal is obtained comprehensively according to prediction probabilities outputted by the classifier, the margin discriminator, and the condition discriminator, so that the electroencephalogram signal classification model can recognize electroencephalogram signals of different types, to improve accuracy of the motor imagery type outputted by the electroencephalogram signal classification model.

The signal feature of the electroencephalogram signal is outputted by invoking each layer structure in a feature extraction model, so that the signal feature of the electroencephalogram signal has time invariance, and subsequently the electroencephalogram signal classification model outputs an accurate motor imagery type.

The apparatus for classifying an electroencephalogram signal provided in the foregoing embodiments is illustrated with an example of division of the foregoing functional modules. The functions may be allocated to and completed by different functional modules or code according to requirements, that is, the internal structure of the apparatus is divided into different functional modules or code, to implement all or some of the functions described above. In addition, the apparatus for classifying an electroencephalogram signal provided in the foregoing embodiment belongs to the same concept as the embodiment of the method for classifying an electroencephalogram signal, and for the specific implementation process of the apparatus, refer to the method embodiment, and details are not described herein again.

FIG. 10 is a structural block diagram of an apparatus for training an electroencephalogram signal classification model according to an example embodiment of the disclosure. The apparatus may be implemented as an entire computer device or a part of the computer device. The apparatus includes the following:

a second obtaining module 1010 configured to obtain a source domain electroencephalogram signal and a target domain electroencephalogram signal;

a second feature extraction module 1020 configured to perform feature extraction on the source domain electroencephalogram signal and the target domain electroencephalogram signal to obtain a source domain feature corresponding to the source domain electroencephalogram signal and a target domain feature corresponding to the target domain electroencephalogram signal;

the second obtaining module 1010 being configured to obtain a difference distribution ratio, the difference distribution ratio being used for representing impacts of difference distributions of different types on distributions of the source domain feature and the target domain feature in a feature domain;

a second processing module 1030 configured to align the source domain feature with the target domain feature in the feature domain according to the difference distribution ratio to obtain an aligned target domain feature; and a training module 1040 configured to classify the aligned target domain feature, and train an electroencephalogram signal classification model according to a classification result to obtain a trained electroencephalogram signal classification model.

In an example embodiment, the difference distribution ratio may include a first distribution ratio corresponding to a marginal distribution difference and a second distribution ratio corresponding to a conditional distribution difference.

The second obtaining module 1010 is configured to obtain the marginal distribution difference and the conditional distribution difference between the source domain feature and the target domain feature in the feature domain.

The second processing module 1030 is configured to scale down the marginal distribution difference according to the first distribution ratio and scale down the conditional distribution difference according to the second distribution ratio; obtain a signal feature with a scaled-down distribution difference according to a scaled-down marginal distribution difference and a scaled-down conditional distribution difference; and determine the target domain feature with the scaled-down distribution difference as the aligned target domain feature.

In an example embodiment, the second obtaining module 1010 is configured to obtain first classification accuracy of a margin discriminator and second classification accuracy of a condition discriminator, the margin discriminator being configured to determine a domain signal to which the electroencephalogram signal belongs, the condition discriminator being configured to determine, according to the motor imagery type, a domain signal to which electroencephalogram signals of different types belong, and the domain signal including at least one of the source domain electroencephalogram signal or the target domain electroencephalogram signal; obtain a first distribution distance between the target domain feature and the source domain feature according to the first classification accuracy, and obtain a second distribution distance between the target domain feature and the source domain feature according to the second classification accuracy; and determine the first distribution distance as the marginal distribution difference, and determine the second distribution distance as the conditional distribution difference.

In an example embodiment, the apparatus may include an electroencephalogram signal classification model 1050.

The electroencephalogram signal classification model 1050 is configured to invoke a classifier, a margin discriminator, and a condition discriminator to respectively process the aligned target domain feature, to obtain a prediction probability of a motor imagery type corresponding to the target domain electroencephalogram signal.

The training module 1040 is configured to calculate a result error of the electroencephalogram signal classification model according to the prediction probability and a real label of the motor imagery type corresponding to the electroencephalogram signal; and train the electroencephalogram signal classification model according to the result error and by using an error back propagation algorithm, to obtain the trained electroencephalogram signal classification model.

In an example embodiment, the training module 1040 may be configured to calculate a first loss function corresponding to the classifier according to the prediction probability and the real label; calculate a second loss function corresponding to the condition discriminator according to a source domain condition feature map corresponding to the source domain feature and a target domain condition feature map corresponding to the target domain feature that are outputted by the condition discriminator; calculate a third loss function corresponding to the margin discriminator according to a source domain feature map corresponding to the source domain feature and a target domain feature map corresponding to the target domain feature that are outputted by the margin discriminator; and calculate the result error of the electroencephalogram signal classification model according to the first loss function, the second loss function, and the third loss function.

Based on the foregoing, according to the apparatus provided in this embodiment, a distribution of a target domain feature in a feature domain is dynamically adjusted according to a difference distribution ratio, to align the target domain feature with a source domain feature, so as to train an electroencephalogram signal classification model based on an aligned target domain feature, so that the electroencephalogram signal classification model can transfer a classification learning method to the target domain feature, and the trained electroencephalogram signal classification model can accurately output a motor imagery type corresponding to an electroencephalogram signal and recognize a plurality of types of electroencephalogram signals, thereby achieving universality.

A distribution difference between the target domain feature and the source domain feature that are inputted into the electroencephalogram signal classification model is dynamically adjusted according to a first distribution ratio corresponding to a marginal distribution difference and a second distribution ratio corresponding to a conditional distribution difference, so that the target domain feature is accurately close to the source domain feature, thereby ensuring that the electroencephalogram signal classification model can accurately obtain an aligned target domain feature.

A first distribution distance and a second distribution distance between the source domain feature and the target domain feature are determined according to first classification accuracy of a margin discriminator and second classification accuracy of a condition discriminator, so that the electroencephalogram signal classification model determines the marginal distribution difference and the conditional distribution difference according to the first distribution distance and the second distribution distance.

The aligned target domain feature is processed by using a classifier, the margin discriminator, and the condition discriminator, and the electroencephalogram signal classification model is trained by using a real label of the motor imagery type corresponding to the electroencephalogram signal and an error between prediction probabilities outputted by the electroencephalogram signal classification model, to ensure that the electroencephalogram signal classification model may accelerate convergence, thereby shortening a training time of the model.

A result error of the electroencephalogram signal classification model is accurately calculated according to a first loss function corresponding to the classifier, a second loss function corresponding to the margin discriminator, and a third loss function corresponding to the condition discriminator, so that the electroencephalogram signal classification model is trained based on the accurate result error, to improve a convergence speed of the model, thereby shortening the training time of the model.

The apparatus for training an electroencephalogram signal classification model provided in the foregoing embodiments is illustrated with an example of division of the foregoing functional modules. The functions may be allocated to and completed by different functional modules or code according to requirements, that is, the internal structure of the apparatus is divided into different functional modules or code to implement all or some of the functions described above. In addition, the apparatus for training an electroencephalogram signal classification model provided in the foregoing embodiment belongs to the same concept as the embodiment of the method for training an electroencephalogram signal classification model, and for the specific implementation process of the apparatus, refer to the method embodiment, and details are not described herein again.

Figure 11:
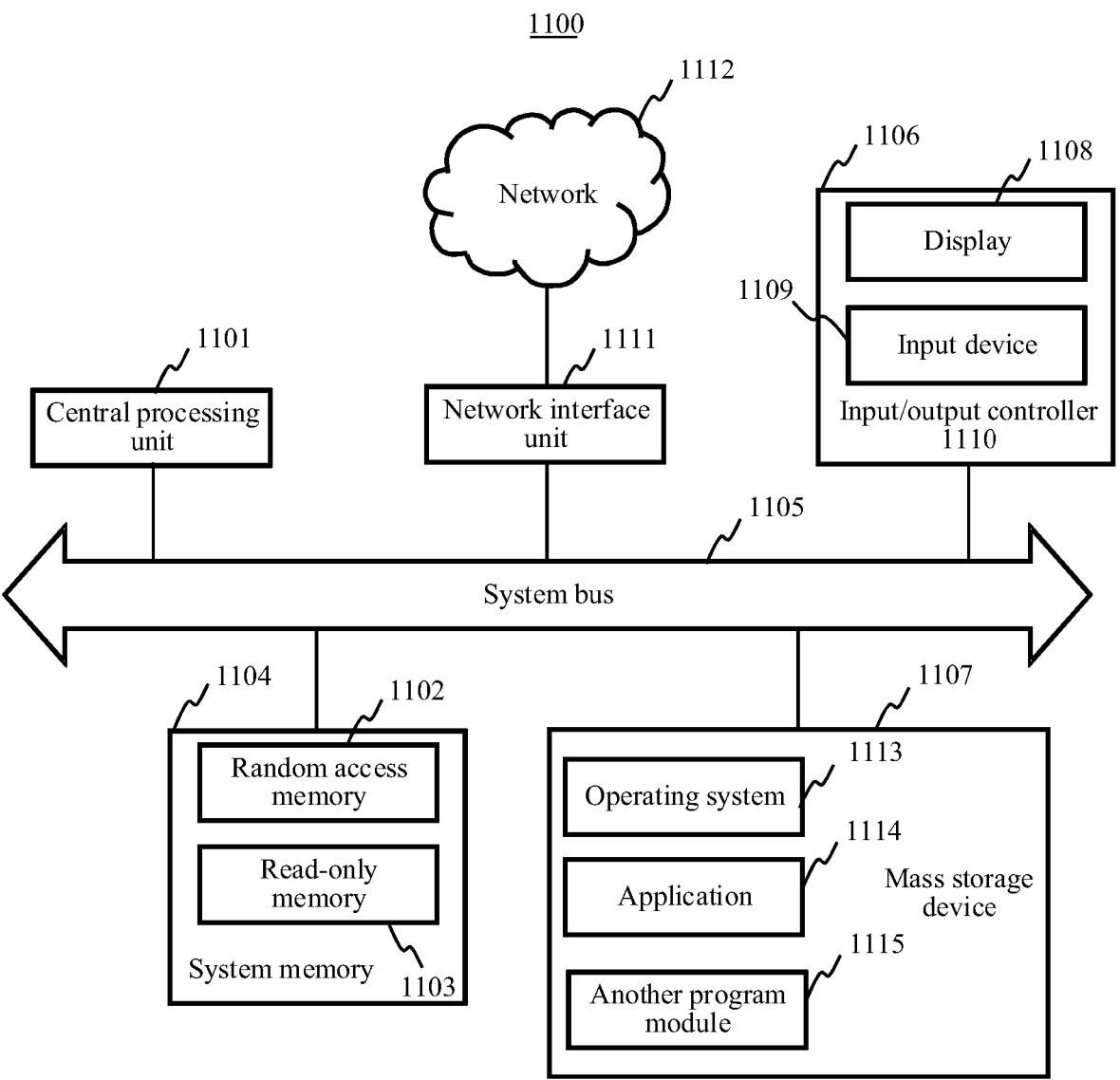
FIG. 11 is a schematic diagram of a structure of an apparatus of a server according to an example embodiment of the disclosure.

FIG. 11 is a schematic structural diagram of a server according to an example embodiment of the disclosure. The server may be the server 120 in the computer system 100 shown in FIG. 1.

A server 1100 includes a central processing unit (CPU) 1101, a random access memory (RAM) 1102, a system memory 1104 of a read only memory (ROM) 1103, and a system bus 1105 connecting the system memory 1104 to the CPU 1101. The server 1100 further includes a basic input/output (I/O) system 1106 assisting in transmitting information between devices in a computer, and a mass storage device 1107 configured to store an operating system 1113, an application program 1114 and another program module 1115.

The basic I/O system 1106 includes a display 1108 configured to display information and an input device 1109 such as a mouse or a keyboard configured to input information by a user. The display 1108 and the input device 1109 are both connected to the CPU 1101 by using an input/output controller 1110 that is connected to the system bus 1105. The basic I/O system 1106 may further include the I/O controller 1110 configured to receive and process input from a plurality of other devices such as a keyboard, a mouse, or an electronic stylus. Similarly, the I/O controller 1110 further provides an output to a display screen, a printer, or another type of output device.

The mass storage device 1107 is connected to the CPU 1101 by using a mass storage controller (not shown) connected to the system bus 1105. The mass storage device 1107 and a computer-readable medium associated with the mass storage device provide non-volatile storage for the server 1100. That is, the mass storage device 1107 may include a computer-readable medium (not shown) such as a hard disk or a compact disc read only memory (CD-ROM) drive.

The computer-readable medium may include a computer storage medium and a communication medium. The computer-storage medium includes volatile and non-volatile media, transitory and non-transitory, and removable and non-removable media implemented by using any method or technology used for storing information such as computer-readable instructions, data structures, program modules, program code or other data. The computer storage medium includes a RAM, a ROM, an erasable programmable ROM (EPROM), an electrically erasable programmable ROM (EEPROM), a flash memory or another solid-state memory technology, a CD-ROM, a digital versatile disc (DVD) or a solid state drive (SSD), another optical memory, a magnetic cassette, a magnetic tape, a magnetic disk memory, or another magnetic storage device. The RAM may include a resistance random access memory (ReRAM) and a dynamic random access memory (DRAM). A person skilled in the art may know that the computer storage medium is not limited to the foregoing types. The system memory 1104 and the mass storage device 1107 may be collectively referred to as a memory.

According to various embodiments of the disclosure, the server 1100 may further be connected, by using a network such as the Internet, to a remote computer on the network and run. That is, the server 1100 may be connected to a network 1112 by using a network interface unit 1111 that is connected to the system bus 1105, or may be connected to a network of another type or a remote computer system (not shown) by using the network interface unit 1111.

The memory further includes one or more programs, which are stored in the memory and are configured to be executed by the CPU.

In an example embodiment, a computer device may be provided, including a processor and a memory, the memory storing at least one instruction, at least one program, a code set or an instruction set, the at least one instruction, the at least one program, the code set or the instruction set being loaded and executed by the processor to implement at least one of the method for classifying an electroencephalogram signal or the method for training an electroencephalogram signal classification model.

In an example embodiment, a computer-readable storage medium may be provided, storing at least one instruction, at least one program, a code set or an instruction set, the at least one instruction, the at least one program, the code set or the instruction set being loaded and executed by a processor to implement at least one of the method for classifying an electroencephalogram signal or the method for training an electroencephalogram signal classification model.

The computer-readable storage medium may include: a ROM, a RAM, a solid state drive (SSD), an optical disc, or the like. The RAM may include a resistance random access memory (ReRAM) and a dynamic random access memory (DRAM). The sequence numbers of the foregoing embodiments of the disclosure are only for description purpose, and are not intended to indicate the preference among the embodiments.

An embodiment of the disclosure provides a computer program product or a computer program. The computer program product or the computer program includes computer instructions, and the computer instructions are stored in a computer readable storage medium. A processor of the computer device reads the computer instructions from the computer-readable storage medium and executes the computer instructions to cause the computer device to perform at least one of the method for classifying an electroencephalogram signal or the method for training an electroencephalogram signal classification model.

After considering the specification and practicing the disclosed embodiments, a person skilled in the art may easily conceive of other embodiments of the disclosure. The disclosure is intended to cover any variations, uses, or adaptive changes of the disclosure following the general principles of the disclosure, and includes well-known knowledge and conventional technical means in the art and undisclosed in the disclosure.

It is to be understood that the disclosure is not limited to the precise structures described above and shown in the accompanying drawings, and various modifications and changes may be made without departing from the scope of the disclosure.

What is claimed is:

1. A method for classifying an electroencephalogram signal, performed by a computer device, the method comprising:
obtaining, via an electroencephalogram signal device and configured to connect to a terminal executing a game application, an electroencephalogram signal associated with the game application, the electroencephalogram signal device establishing a brain computer interface (BCI) between the electroencephalogram signal device and a user wearing the electroencephalogram signal device to acquire motor imagery of the user;
performing feature extraction on the electroencephalogram signal to obtain a signal feature corresponding to the electroencephalogram signal;
obtaining a difference distribution ratio, the difference distribution ratio being used for representing impacts of difference distributions of different types on distributions of the signal feature and a source domain feature in a feature domain, the source domain feature being a feature corresponding to a source domain electroencephalogram signal;
aligning the signal feature with the source domain feature according to the difference distribution ratio to obtain an aligned signal feature;

classifying the aligned signal feature to obtain a motor imagery type of the motor imagery of the user corresponding to the electroencephalogram signal; and executing control of the game application based on at least the motor imagery type.

2. The method according to claim 1, wherein the difference distribution ratio comprises a first distribution ratio corresponding to a marginal distribution difference and a second distribution ratio corresponding to a conditional distribution difference; and the aligning comprises:

obtaining the marginal distribution difference and the conditional distribution difference between the source domain feature and the signal feature in the feature domain;

scaling down the marginal distribution difference according to the first distribution ratio, and scaling down the conditional distribution difference according to the second distribution ratio;

obtaining a signal feature with a scaled-down distribution difference according to a scaled-down marginal distribution difference and a scaled-down conditional distribution difference; and determining the signal feature with the scaled-down distribution difference as the aligned signal feature.

3. The method according to claim 2, wherein the obtaining the marginal distribution difference and the conditional distribution difference between the source domain feature and the signal feature in the feature domain comprises:

obtaining first classification accuracy of a margin discriminator and second classification accuracy of a condition discriminator, the margin discriminator being configured to determine a domain signal to which the electroencephalogram signal belongs, the condition discriminator being configured to determine a domain signal to which electroencephalogram signals of different types belong, and the domain signal comprising at least one of the source domain electroencephalogram signal or an inputted electroencephalogram signal;

obtaining a first distribution distance between the signal feature and the source domain feature according to the first classification accuracy, and obtaining a second distribution distance between the signal feature and the source domain feature according to the second classification accuracy; and determining the first distribution distance as the marginal distribution difference, and determining the second distribution distance as the conditional distribution difference.

4. The method according to claim 1, wherein the difference distribution ratio comprises the first distribution ratio corresponding to the marginal distribution difference and the second distribution ratio corresponding to the conditional distribution difference; and the obtaining a difference distribution ratio comprises:

obtaining the first distribution distance and the second distribution distance between the signal feature and the source domain feature, the first distribution distance being used for representing the marginal distribution difference between the signal feature and the source domain feature, and the second distribution distance being used for representing the conditional distribution difference between the signal feature and the source domain feature;

obtaining a type quantity of motor imagery types; and obtaining the first distribution ratio corresponding to the marginal distribution difference and the second distribution ratio corresponding to the conditional distribution difference according to the first distribution distance, the second distribution distance, and the type quantity.

5. The method according to claim 1, wherein the classifying comprises:

invoking a classifier to process the aligned signal feature, to obtain a prediction probability of the motor imagery type corresponding to the electroencephalogram signal;

invoking the condition discriminator to process the aligned signal feature, to obtain prediction probabilities that the electroencephalogram signals of different types belong to the domain signal, the domain signal comprising at least one of the source domain electroencephalogram signal or the inputted electroencephalogram signal;

invoking the margin discriminator to process the aligned signal feature, to obtain a prediction probability that the electroencephalogram signal belongs to the domain signal; and obtaining the motor imagery type corresponding to the electroencephalogram signal according to the prediction probability of the motor imagery type corresponding to the electroencephalogram signal, the prediction probabilities that the electroencephalogram signals of different types belong to the domain signal, and the prediction probability that the electroencephalogram signal belongs to the domain signal.

6. The method according to claim 1, wherein the performing comprises:

invoking a temporal convolutional layer to perform feature extraction on the electroencephalogram signal, to obtain a first signal feature corresponding to the electroencephalogram signal;

invoking a spatial convolutional layer to perform feature extraction on the first signal feature, to obtain a second signal feature corresponding to the electroencephalogram signal;

invoking a batch normalization layer to perform feature extraction on the second signal feature to obtain a third signal feature corresponding to the electroencephalogram signal;

invoking a square activation layer to perform feature extraction on the third signal feature, to obtain a fourth signal feature corresponding to the electroencephalogram signal;

invoking an average pooling layer to perform feature extraction on the fourth signal feature, to obtain a fifth signal feature corresponding to the electroencephalogram signal; and invoking a dropout layer to perform feature extraction on the fifth signal feature to obtain a sixth signal feature corresponding to the electroencephalogram signal, and determining the sixth signal feature as the signal feature corresponding to the electroencephalogram signal.

7. The method according to claim 2, wherein the marginal distribution difference and the conditional distribution difference are scaled down simultaneously.

8. An apparatus for classifying an electroencephalogram signal comprising:

at least one memory configured to store program code; and at least one processor configured to read the program code and operate as instructed by the program code, the program code comprising:

first obtaining code configured to cause the at least one processor to obtain, via an electroencephalogram signal acquisition device and configured to connect to a terminal executing a game application, an electroencephalogram signal associated with the game application, the electroencephalogram signal device establishing a brain computer interface (BCI) between the electroencephalogram signal device and a user wearing the electroencephalogram signal device to acquire motor imagery of the user;

first feature extraction code configured to cause the at least one processor to perform feature extraction on the electroencephalogram signal, to obtain a signal feature corresponding to the electroencephalogram signal;

the first obtaining code being configured to cause the at least one processor to obtain a difference distribution ratio, the difference distribution ratio being used for representing impacts of difference distributions of different types on distributions of the signal feature and a source domain feature in a feature domain, the source domain feature being a feature corresponding to a source domain electroencephalogram signal;

first processing code configured to cause the at least one processor to align the signal feature with the source domain feature according to the difference distribution ratio, to obtain an aligned signal feature;

classification code configured to cause the at least one processor to classify the aligned signal feature to obtain a motor imagery type of the motor imagery of the user corresponding to the electroencephalogram signal; and control code configured to cause the at least one processor to execute control of the game application based on at least the motor imagery type.

9. The apparatus according to claim 8, wherein the difference distribution ratio comprises a first distribution ratio corresponding to a marginal distribution difference and a second distribution ratio corresponding to a conditional distribution difference; and the first processing code is further configured to cause the at least one processor to:

obtain the marginal distribution difference and the conditional distribution difference between the source domain feature and the signal feature in the feature domain;

scale down the marginal distribution difference according to the first distribution ratio, and scale down the conditional distribution difference according to the second distribution ratio;

obtain a signal feature with a scaled-down distribution difference according to a scaled-down marginal distribution difference and a scaled-down conditional distribution difference; and determine the signal feature with the scaled-down distribution difference as the aligned signal feature.

10. The apparatus according to claim 9, wherein the first processing code is further configured to cause the at least one processor to:

obtain first classification accuracy of a margin discriminator and second classification accuracy of a condition discriminator, the margin discriminator being configured to determine a domain signal to which the electroencephalogram signal belongs, the condition discriminator being configured to determine a domain signal to which electroencephalogram signals of different types belong, and the domain signal comprising at least one of the source domain electroencephalogram signal or an inputted electroencephalogram signal;

obtain a first distribution distance between the signal feature and the source domain feature according to the first classification accuracy, and obtain a second distribution distance between the signal feature and the source domain feature according to the second classification accuracy; and determine the first distribution distance as the marginal distribution difference, and determine the second distribution distance as the conditional distribution difference.

11. The apparatus according to claim 8, wherein the difference distribution ratio comprises the first distribution ratio corresponding to the marginal distribution difference and the second distribution ratio corresponding to the conditional distribution difference; and the first obtaining code is further configured to cause the at least one processor to:

obtain the first distribution distance and the second distribution distance between the signal feature and the source domain feature, the first distribution distance being used for representing the marginal distribution difference between the signal feature and the source domain feature, and the second distribution distance being used for representing the conditional distribution difference between the signal feature and the source domain feature;

obtain a type quantity of motor imagery types; and obtain the first distribution ratio corresponding to the marginal distribution difference and the second distribution ratio corresponding to the conditional distribution difference according to the first distribution distance, the second distribution distance, and the type quantity.

12. The apparatus according to claim 8, wherein the clarification code is further configured to cause the at least one processor to:

invoke a classifier to process the aligned signal feature to obtain a prediction probability of the motor imagery type corresponding to the electroencephalogram signal;

invoke the condition discriminator to process the aligned signal feature to obtain prediction probabilities that the electroencephalogram signals of different types belong to the domain signal, the domain signal comprising at least one of the source domain electroencephalogram signal or the inputted electroencephalogram signal;

invoke the margin discriminator to process the aligned signal feature to obtain a prediction probability that the electroencephalogram signal belongs to the domain signal; and obtain the motor imagery type corresponding to the electroencephalogram signal according to the prediction probability of the motor imagery type corresponding to the electroencephalogram signal, the prediction probabilities that the electroencephalogram signals of different types belong to the domain signal, and the prediction probability that the electroencephalogram signal belongs to the domain signal.

13. The apparatus according to claim 8, wherein the first feature extraction code is further configured to cause the at least one processor to:

invoke a temporal convolutional layer to perform feature extraction on the electroencephalogram signal to obtain a first signal feature corresponding to the electroencephalogram signal;

invoke a spatial convolutional layer to perform feature extraction on the first signal feature to obtain a second signal feature corresponding to the electroencephalogram signal;

invoke a batch normalization layer to perform feature extraction on the second signal feature to obtain a third signal feature corresponding to the electroencephalogram signal;

invoke a square activation layer to perform feature extraction on the third signal feature to obtain a fourth signal feature corresponding to the electroencephalogram signal;

invoke an average pooling layer to perform feature extraction on the fourth signal feature to obtain a fifth signal feature corresponding to the electroencephalogram signal; and invoke a dropout layer to perform feature extraction on the fifth signal feature to obtain a sixth signal feature corresponding to the electroencephalogram signal, and determine the sixth signal feature as the signal feature corresponding to the electroencephalogram signal.

14. The apparatus according to claim 9, wherein the marginal distribution difference and the conditional distribution difference are scaled down simultaneously.

15. A non-transitory computer-readable storage medium, storing computer program code that when executed by at least one processor causes the at least one processor to:

obtain, via an electroencephalogram signal device and configured to connect to a terminal executing a game application, an electroencephalogram signal associated with the game application, the electroencephalogram signal device establishing a brain computer interface (BCI) between the electroencephalogram signal device and a user wearing the electroencephalogram signal device to acquire motor imagery of the user;

perform feature extraction on the electroencephalogram signal to obtain a signal feature corresponding to the electroencephalogram signal;

obtain a difference distribution ratio, the difference distribution ratio being used for representing impacts of difference distributions of different types on distributions of the signal feature and a source domain feature in a feature domain, the source domain feature being a feature corresponding to a source domain electroencephalogram signal;

align the signal feature with the source domain feature according to the difference distribution ratio to obtain an aligned signal feature;

classify the aligned signal feature to obtain a motor imagery type of the motor imagery of the user corresponding to the electroencephalogram signal; and execute control of the game application based on at least the motor imagery type.

16. The non-transitory computer-readable storage medium according to claim 15, wherein the difference distribution ratio comprises a first distribution ratio corresponding to a marginal distribution difference and a second distribution ratio corresponding to a conditional distribution difference; and the aligning comprises:

obtaining the marginal distribution difference and the conditional distribution difference between the source domain feature and the signal feature in the feature domain;

scaling down the marginal distribution difference according to the first distribution ratio, and scaling down the conditional distribution difference according to the second distribution ratio;

obtaining a signal feature with a scaled-down distribution difference according to a scaled-down marginal distribution difference and a scaled-down conditional distribution difference; and determining the signal feature with the scaled-down distribution difference as the aligned signal feature.

17. The non-transitory computer-readable storage medium according to claim 16, wherein the obtain the marginal distribution difference and the conditional distribution difference between the source domain feature and the signal feature in the feature domain comprises:

obtaining first classification accuracy of a margin discriminator and second classification accuracy of a condition discriminator, the margin discriminator being configured to determine a domain signal to which the electroencephalogram signal belongs, the condition discriminator being configured to determine a domain signal to which electroencephalogram signals of different types belong, and the domain signal comprising at least one of the source domain electroencephalogram signal or an inputted electroencephalogram signal;

obtaining a first distribution distance between the signal feature and the source domain feature according to the first classification accuracy, and obtaining a second distribution distance between the signal feature and the source domain feature according to the second classification accuracy; and determining the first distribution distance as the marginal distribution difference, and determining the second distribution distance as the conditional distribution difference.

18. The non-transitory computer-readable storage medium according to claim 15, wherein the difference distribution ratio comprises the first distribution ratio corresponding to the marginal distribution difference and the second distribution ratio corresponding to the conditional distribution difference; and the obtain a difference distribution ratio comprises:

obtaining the first distribution distance and the second distribution distance between the signal feature and the source domain feature, the first distribution distance being used for representing the marginal distribution difference between the signal feature and the source domain feature, and the second distribution distance being used for representing the conditional distribution difference between the signal feature and the source domain feature;

obtaining a type quantity of motor imagery types; and obtaining the first distribution ratio corresponding to the marginal distribution difference and the second distribution ratio corresponding to the conditional distribution difference according to the first distribution distance, the second distribution distance, and the type quantity.

19. The non-transitory computer-readable storage medium according to claim 15, wherein the classifying comprises:

invoking a classifier to process the aligned signal feature, to obtain a prediction probability of the motor imagery type corresponding to the electroencephalogram signal;

invoking the condition discriminator to process the aligned signal feature, to obtain prediction probabilities that the electroencephalogram signals of different types belong to the domain signal, the domain signal comprising at least one of the source domain electroencephalogram signal or the inputted electroencephalogram signal;

invoking the margin discriminator to process the aligned signal feature, to obtain a prediction probability that the electroencephalogram signal belongs to the domain signal; and obtaining the motor imagery type corresponding to the electroencephalogram signal according to the prediction probability of the motor imagery type corresponding to the electroencephalogram signal, the prediction probabilities that the electroencephalogram signals of different types belong to the domain signal, and the prediction probability that the electroencephalogram signal belongs to the domain signal.

20. The non-transitory computer-readable storage medium according to claim 15, wherein the performing comprises:

invoking a temporal convolutional layer to perform feature extraction on the electroencephalogram signal, to obtain a first signal feature corresponding to the electroencephalogram signal;

invoking a spatial convolutional layer to perform feature extraction on the first signal feature, to obtain a second signal feature corresponding to the electroencephalogram signal;

invoking a batch normalization layer to perform feature extraction on the second signal feature, to obtain a third signal feature corresponding to the electroencephalogram signal;

invoking a square activation layer to perform feature extraction on the third signal feature, to obtain a fourth signal feature corresponding to the electroencephalogram signal;

invoking an average pooling layer to perform feature extraction on the fourth signal feature, to obtain a fifth signal feature corresponding to the electroencephalogram signal; and invoking a dropout layer to perform feature extraction on the fifth signal feature, to obtain a sixth signal feature corresponding to the electroencephalogram signal, and determining the sixth signal feature as the signal feature corresponding to the electroencephalogram signal.

* * * * *